United States Patent [19]

Lerner et al.

[11] Patent Number: 5,429,941
[45] Date of Patent: Jul. 4, 1995

[54] PROCESS FOR ANTIBODY COMBINING SITE-CATALYZED EPOXIDE FORMATION FROM 1-BENZYL-1-HYDROCARBYL ALKENE MOLECULES

[76] Inventors: Richard A. Lerner, 7750 E. Roseland Dr., La Jolla, Calif. 92037; Andreas Koch, 13850 Mango Dr., #38; Jean-Louis Reymond, 13546 Mango Dr., both of Del Mar, all of Calif. 92014

[21] Appl. No.: 186,002

[22] Filed: Jan. 24, 1994

[51] Int. Cl.6 .......................... C12P 17/02; C12N 9/00
[52] U.S. Cl. ................................... 435/123; 435/188.5
[58] Field of Search ....................... 435/188.5, 118, 123

[56] References Cited

PUBLICATIONS

Reymond, Jr., et al, (1992) J. Am. Chem. Soc. 114, 2257–2258.
Reymond, Jr., et. al. (1994) Angew. Chem, Int. Ed. Engl. 33(4), 475–477.
Sinha, S. C, et. al, (1993) Proc. Natl. Acad. Sci, USA. 90, 11910–11913.
Reymond, J. L, et. al. (1991) Angew. Chem. Ed. Engl. 30 (12), 1711–1713.
Reymond, J. L., et. al. (1993) J. Am. Chem. Soc. 115, 3907–3917.
Sinha, S. C., et. al. (1993) J. Am. Chem. Soc. 115, 4893–4894.

*Primary Examiner*—Charles L. Patterson, Jr.
*Attorney, Agent, or Firm*—Welsh & Katz, Ltd.

[57] ABSTRACT

A process is disclosed by which a 1-benzyl-1-hydrocarbyl alkene substrate is catalytically converted to an epoxide. The catalyst is a monoclonal antibody or paratope-containing molecule that binds to the substrate as well as to an N-benzyl-N-hydrocarbylpiperidinium compound that is an analog to the substrate. The chemical reaction is carried out in an aqueous medium using a peroxycarboximic acid as the oxidant.

10 Claims, No Drawings

PROCESS FOR ANTIBODY COMBINING SITE-CATALYZED EPOXIDE FORMATION FROM 1-BENZYL-1-HYDROCARBYL ALKENE MOLECULES

DESCRIPTION

1. Technical Field

The present invention relates to antibodies, antigens and immunogens, and more particularly to a process that utilizes paratope-containing molecules that catalyze epoxide formation from a 1-benzyl-1-hydrocarbyl alkene molecule.

2. Background of the Invention

Binding phenomena between ligands and receptors play many crucial roles in biological systems. Exemplary of such phenomena are the binding of oxygen molecules to deoxyhemoglobin to form oxyhemoglobin, and the binding of a substrate to an enzyme that acts upon it such as between a protein and a protease like trypsin (EC 3.4.21.4) or between (S)-2,3-epoxysqualene and lanosterol synthase (EC 5.4.99.7) in the formation of lanosterol. Still further examples of biological binding phenomena include the binding of an antigen to an antibody, and the binding of complement component C3 to the so-called CR1 receptor.

Many drugs and other therapeutic agents are also believed to be dependent upon binding phenomena. For example, opiates such as morphine are reported to bind to specific receptors in the brain. Opiate agonists and antagonists are reported to compete with drugs like morphine for those binding sites.

Ligands such as man-made drugs, like morphine and its derivatives, and those that are naturally present in biological systems such as endorphins and hormones bind to receptors that are naturally present in biological systems, and will be treated together herein. Such binding can lead to a number of the phenomena of biology, including particularly the hydrolysis of amide and ester bonds as where proteins are hydrolyzed into constituent polypeptides by an enzyme such as trypsin or papain, or where a fat is cleaved into glycerine and three carboxylic acids, respectively.

Slobin, *Biochemistry*, 5:2836-2844 (1966) reported preparing antibodies to a p-nitrocarbobenzoxy conjugate of bovine serum albumin. Those antibodies were thereafter used to hydrolyze p-nitrophenyl acetate and epsilon-aminocaproate esters. The reaction of the acetate ester was described by a second-order rate constant and was said to appear to be nonspecific. The second-order rate constant obtained using normal gamma globulin was said to be about equal to that of the specially prepared antibodies. The presence of the specially prepared antibodies was said to inhibit the hydrolysis of the aminocaproate ester.

Kohnen and coworkers also reported attempts using antibodies to catalyze esterolysis. The antibodies utilized by this group were, in each instance, raised to a portion of the ultimately utilized substrate molecule that did not contain the bond to be hydrolyzed.

In their initial work [*FEBS Letters*, 100:137-140 (1979) and *Biochim. Biophys. Acta*, 629:328-337 (1980)] anti-steroid antibodies were used to hydrolyze 7-umbelliferone (7-hydroxycoumerin) esters of a carboxyethyl thioether of asteroid. In each instance, an increase in hydrolyric rate was observed as compared to background or to a rate obtained with normal IgG. In both instances, turnover numbers were low (about one mole of substrates per mole of antibody per minute, or less), and the reaction rates declined with time, reaching a plateau with saturation of the antibody. That slow down in rate was attributed to an irreversible binding of the steroidal acid product to the antibody.

Kohen et al. also reported hydrolysis of 7-[-N-(2,4-dinitrophenyl)-6-aminohexanoyl]-coumerin using monoclonal antibodies raised to the dinitrophenyl portions of that substrate molecule [*FEBS Letters*, 111:427-431 (1980)]. Here, a rate increase over background was also reported, but the reaction was said to be stoichiometric rather than catalytic. A decrease in rate that approached zero was reported as saturation of the antibody was reached. Again, the decrease was attributed to product inhibition caused by binding of the product acid to the antibody since some of the initial hydrolysis activity could be regenerated by chromatography of an antibody-substrate-product mixture.

When strong antibody binding is directed to stable states of substrate molecules, the slow rate of dissociation of the complex impedes catalysis. Such is thought to be the situation for the results reported by Kohnen and coworkers.

The above constructs, though interesting, are severely limited by the failure to address the mechanism of binding energy utilization that is essential to enzymes [W. P. Jencks, *Adv. Enzymol.*, 43, 219 (1975)].

Those deficiencies can be redressed by using a transition state analog as the hapten to elicit the desired antibodies. This hapten (also referred to herein as an "analog ligand") can assume the role of an inhibitor in the catalytic system.

Thus, immunological binding can be used to divert binding interactions to catalytic processes. For example, it was suggested that use of an antibody to a haptenic group that resembles the transition state of a given reaction should cause an acceleration in substrate reaction by forcing substrates to resemble the transition state. Jencks, W.P., *Catalysis in Chemistry and Enzymology*, page 288 (McGraw-Hill, New York 1969). Notwithstanding that broad suggestion, specific transition state haptens were not suggested, nor were specific reactions suggested in which the concept might be tested.

Hydrolysis of amide and ester bonds is thought by presently accepted chemical theory to proceed in aqueous media by a reaction at the carbonyl carbon atom to form a transition state that contains a tetrahedral carbon atom bonded to (a) a carbon atom of the acid portion of the amide or ester, (b) two oxygen atoms, one being from the carbonyl group and the other from a hydroxyl ion or water molecule of the medium, and (c) the oxygen atom of the alcohol portion of an ester or the nitrogen atom of the amine portion of an amide. Transition states of such reactions are useful mental constructs that by definition, cannot be isolated, as compared to intermediates, which are isolatable.

Although the above hydrolyric transition states cannot be isolated, a large amount of scientific literature has been devoted to the subject. Some of that literature is discussed hereinafter.

Whereas the before-described transition state for amide and ester hydrolyses is believed to be well understood, the parameters of the topology, e.g., size, shape and charge, of receptor binding sites in which particular amides, such as proteins, or esters, such as fats, react through those transition states is not as well understood.

It would therefore be beneficial if the topology of a plurality of binding sites were known so that the interactions of the ligands that bind in those sites could be studied. Unfortunately, the topology of receptor binding sites in the well-studied field of biological hydrolyses is generally unknown, except for a relatively small number of enzymes whose X-ray crystal structures have been determined.

This lack of knowledge of binding site topology stems in part from a lack of knowledge of even the location in cells of many binding sites of receptors. In addition, for those receptor binding sites whose location is known, the chemical identity, i.e., protein and carbohydrate composition, of the binding site is generally unknown. Thus, the investigator is generally stymied in seeking to understand the topological requirements of receptor binding sites and therefore in seeking to construct therapeutic agents that can fulfill those requirements.

Investigators must therefore screen potential therapeutic agents in animal or cell culture studies to ascertain whether a potential therapeutic agent may be useful. Such systems, while useful, are expensive and time-consuming to use.

Even where the topology and chemical reactivity of a hydrolyric receptor such as an enzyme are known, enzymes such as hydrolyric proteases typically cleave their substrates, polypeptide chains, adjacent to a particular amino acid residue that may occur several times in the polypeptide chain of the protein. While such relatively random cleavage can be useful in obtaining a polypeptide map of the protein, that relatively random cleavage is not as useful where particular amino acid residue sequences are desired to be produced.

Recently, Lerner, Tramontano and Janda [*Science*, 234, 1566 (1986)] reported monoclonal antibodies to hydrolyze esters in U.S. Pat. No. 4,656,567. Pollack, Jacobs and Schultz [*Science*, 234, 1570 (1986)] reported a myeloma protein denominated MOPC167 [Leon et al., *Biochem.*, 10, 1424 (1971)] that catalyzes the hydrolysis of a carbonate.

In the two Lerner and Tramontano disclosures, the antibodies were raised to a phosphonate that was synthesized to represent a stable analog of the tetrahedral hydrolyric transition state of the carboxylic acid ester or carbonate ester. The Pollack et al. antibody principally discussed was a myeloma protein that happened to bind to a phosphonate that was structurally analogous to the carbonate analog hydrolyzed. Thus, in the Lerner and Tramontano et al. work, the substrate to be hydrolyzed was preselected, with the immunizing analog and hydrolytic antibodies being synthesized in accordance with the desired product. Pollack et al. designed the substrate to be hydrolyzed once they knew the specificity of the myeloma protein. Pollack et al. also reported (above) the existence of a catalytic antibody, substrated and analog substrate system for carbonate hydrolysis similar in concept to that of Lerner et al. Work relating to that system is reported in Jacobs et al., *J. Am. Chem Soc.*, 109, 2174 (1987).

U.S. Pat. No. 4,888,281 (Schochetman et al.) discusses the possible use of antibodies as catalysts, and presents data relating to the use of polyclonal serum in hydrolyzing o-nitrophenyl-beta-D-galactoside. The antibodies useful in that patent are said to be inducible by a reactant, a reaction intermediate or to an analog of the reactant, product or reaction intermediate. The term "analog" is there defined to encompass isomers, homologs or other compounds sufficiently resembling the reactant in terms of chemical structure that an antibody raised to an analog can participate in an immunological reaction with the reactant but will not necessarily catalyze a reaction of the analog.

The data provided in that specification only indicate that some cleavage of the substrate (reactant) galactoside occurred over an eighteen hour time period using a relatively concentrated antibody preparation (1:10 and 1:20 dilutions). Although catalysis was alleged, catalytic activity was not shown since no turnover of the allegedly catalytic antibody was shown, nor was there an indication of the percentage of substrate galactoside cleaved. The patent did indicate that beta-D-galactosidase cleaved about ten times as much substrate as did the polyclonal antibodies, presuming linearity of absorbance at the unnamed concentration of substrate studied.

From the data presented in that patent, it is possible that a nucleophilic replacement of the o-nitrophenyl group occurred by a terminal amino group of a lysine residue of the antibody preparation used. Thus, the observed absorbance could have been due to formation of epsilon-amino lysinyl o-nitrophenyl aniline or to the formation of an epsilon-amino-lysinyl galactoside and o-nitrophenol, either of which occurrences would not be catalytic since the antibody was consumed, rather than turning over.

U.S. Pat. No. 4,792,446 (Kim et al.) discusses the possible use of antibody catalysts in the synthesis of chiral molecules. However, such syntheses were neither described nor disclosed in that patent.

In more recent work, bimolecular amide formation catalyzed by antibody molecules has been disclosed [Benkovic et al., *Proc. Natl. Acad. Sci. USA*, 85:5355 (1988)], as has an antibody-catalyzed Claisen rearrangement [Jackson et al., *J. Am. Chem. Soc.*, 110:4841 (1988)]. None of that work, nor the previously discussed work, has contemplated the use of antibodies to catalyze any reaction in a stereospecific manner.

Stereospecificity was shown in an antibody-catalyzed lactone-forming reaction [Napper et al., *Science*, 237:1041 (1987)] and in an antibody-catalyzed Claisen reaction [Hilvert et al., *Proc. Natl. Acad. Sci. USA*, 85:4955 (1988)].

U.S. Pat. No. 5,208,152 describes use of catalytic antibodies to catalyze a Dieis-Alder (4+2) cycloaddition reaction. That catalyst binds to two substrate molecules, a conjugated diene and dienophile that react to form an intermediate that itself decomposes to expel a leaving group and form a 5- or 6-membered ring compound.

Antibody molecules were also reported as useful in catalyzing a disfavored cyclization of an epoxyalcohol to form a hydroxytetrahydropyran in Janda et al., *Science*, 259:490–493 (1993). In the latter disclosure, the catalytic antibodies were raised to a 6-membered cyclic N-oxide hapten to presumptively induce complementary charges in the antibody binding pocket while using the binding energy from substrate binding to organize the reaction geometry to favor the desired, disfavored 6-membered ring product over the usually obtained 5-membered ring product in that acid-catalyzed reaction. That acid-catalyzed reaction utilized a regioselective 6-endo-tet ring opening of an epoxide by an internal nucleophilic oxygen atom to form the ring.

BRIEF SUMMARY OF THE INVENTION

The present invention contemplates use of a receptor molecule that is a monoclonal antibody molecule or a molecule that contains an antibody combining site or paratope to catalyze the formation of an epoxide from an ethylenically unsaturated molecule, a 1-benzyl-1-hydrocarbyl alkene. This process comprises the steps of:

(a) admixing in an aqueous medium containing an oxidation-effective amount of a peroxycarboximic acid a catalytically effective amount of monoclonal antibody molecules or paratope-containing portions thereof and a substrate 1-benzyl-1-hydrocarbyl alkene to which the antibody molecules or paratope-containing portions bind to form a reaction medium. The substrate bound by the monoclonal antibody molecules or the paratope-containing portions thereof contains up to about 25 carbon atoms bonded to the carbon atoms of the alkenyl double bond, including the 1-hydrocarbyl substituent and the phenyl ring of the 1-benzyl substituent. The monoclonal antibodies or paratope-containing portions also bind to a structural analog of the substrate. The analog is an N-benzyl-N-hydrocarbylpiperidinium compound in which the nitrogen atom of the piperidinium compound analog ligand is analogous to the 1-carbon atom of the alkene substrate. The analog ligand contains no more ring structures bonded to the piperidinium ring than are present in the substrate. The reaction mixture is maintained (b) under biological reaction conditions for a time period sufficient for the substrate to be converted to a corresponding epoxide.

The formed epoxide is preferably recovered after formation, although recovery is not required as the formed product can be used in situ for the formation of yet another compound such as a diol. These reactions also proceed enantioselectively.

The present invention provides several benefits and advantages. One benefit of the invention is that desired epoxide molecules can be formed at a rate that is faster than is their formation in the absence of monoclonal receptor catalyst.

Another benefit of the present invention is that a desired epoxide compound can be formed in high enantiomeric excess.

An advantage of the invention is that a contemplated process is carried out under-relatively mild oxidation conditions.

Yet another advantage of the present invention is that a desired monoclonal receptor catalyst can be readily prepared.

Still further benefits and advantages of the present invention will be apparent to those skilled in the art from the discussion that follows.

DETAILED DESCRIPTION OF THE INVENTION

I. Introduction

The present invention relates to molecules collectively referred to as receptors that are antibodies or paratope-containing (antibody combining site-containing) portions induced by an analog of a benzyl-hydrocarbyl alkene substrate. The analog ligand mimics the stereochemistry and conformation of the unisolatable transition state in the reaction pathway for the epoxidation of that substrate. The receptor molecules (antibodies and antibody combining sites; i.e., paratope-containing molecules) that bind to the analog ligand and to the benzyl-hydrocarbyl alkene substrate are thought to stabilize the transition state on the reaction pathway between a substrate reactant ligand and epoxide by configurationally orienting the bound substrate into a desired configuration for activating the alkene double bond toward the product-like $sp^3$ hybridization at the homobenzylic carbon, and exhibit catalytic properties in producing a desired product containing an epoxide at the position formerly occupied by the alkene. The product is released from the catalyst after formation.

Antibodies and enzymes are both proteins whose function depends on their ability to bind specific target molecules. Enzymatic reactions differ from immunological reactions in that in an enzymatic reaction the binding of the enzyme to its substrate typically leads to chemical catalysis, whereas a non-catalytic complex is the usual result of antibody-antigen binding.

Enzymes are believed to catalyze reactions such as the hydrolysis of proteins by combining with the protein to stabilize the transition state of the hydrolysis or other reaction. It is generally believed that the rate of an enzymatic reaction is increased relative to the rate of a non-enzymatic reaction because of the ability of the enzyme to stabilize the transition state of the reaction; i.e., to reduce the free energy of the transition state, and thus, the free energy of activation, of the reaction [Jencks, W.P., *Adv. Enzymology*, 43, 219 (1975) and Pauling, L., *Amer. Scientist*, 36, 58 (1948)]. Support for this theory comes from the observation that substances that are thought to model the presumed transition states are often strongly bound to the enzymes as competitive inhibitors. Leinhard, G., *Science*, 180, 149 (1973) and Wolfenden, R., *Acc. Chem. Res.*, 5, 10 (1972). It is further thought that the enzyme accomplishes this lowering of the reaction free energy by binding the transition state geometry-of the reactant more strongly than it binds to the corresponding substrate(s) or product(s).

This means that the intrinsic binding energy of the enzyme is much greater than can be measured from the binding of substrates or products. Essentially, the binding energy of the enzyme is utilized to perform the chemical reaction [Jencks, W.P., *XVII International Solvay Conference* (November 1983)].

The converse proposition is that an antibody that is prepared to optimally bind a suitable analog of a transition state would function as a catalyst. The demonstration of this result by Lerner and co-workers and Schultz and co-workers in the previously cited papers completes the correlation of enzyme function and antibody structure and provides a useful approach to devising artificial enzymes.

The basic idea behind immunological catalysis described herein contemplates the use of analog ligands in the preparation of antibodies of predetermined specificity that preferentially bind to and thereby stabilize the transition state for epoxidation upon binding to the specified substrate reactant ligand. An analog ligand simulates the conformation and the $sp^3$ hybridization of a high energy transition state in an epoxide-forming oxidation to induce the production of antibodies having the ability to bind related substrates and stabilize their epoxide-forming reactions.

Such preferential binding and stabilization results in a reduction in the activation energy for the oxidation reaction, thus meeting a criterion for catalysis. Antibodies that display this property can be obtained by immunization with synthetic analogs that are chemically modified to resemble the size and bonding characteristics of a substrate reactant ligand undergoing epoxidation; i.e., by immunization with transition state analogs of the particular reaction.

In addition, a receptor molecule of the present invention also releases the formed product without itself reacting in a process referred to as turnover so that one antibody molecule can form several product molecules in a given time period. Such turnover meets another criterion for catalysis. It was also particularly surprising that the proteinaceous catalyst molecules were not themselves adversely affected by the oxidant.

The mechanism by which an antibody catalyzes epoxide formation of a bound reactant ligand can be thought of in terms of an "induced fit" model. As the loosely bound substrate distorts or rearranges to conform to the binding geometry induced upon it by the antibody combining site, the alkenyl double bond and its attached at least two 1-position substituents (the benzyl and hydrocarbyl groups) change from their planar, trigonal, configuration of $sp^2$ hybridization toward the pyramidal (tetrahedral) configuration of $sp^3$ hybridization of the epoxide, thereby lowering the activation energy barrier for the oxidation.

The term "receptor" is used herein to mean a molecule that binds to a reactant ligand, inhibitor ligand, or analog ligand. The receptor molecules of the present invention are antibodies or other paratope-containing polyamide portions of an antibody.

Paratope-containing portions (antibody combining sites or idiotypes) of antibodies are those portions of antibody molecules that include the idiotype, and bind to the ligand or analog ligand. Such portions include the Fab, Fab', Fv and F(ab')$_2$ fragments prepared from antibodies by well-known enzymatic cleavage techniques. See for example, U.S. Pat. No. 4,342,566 to Theofilopoulos and Dixon, generally, and specifically, Pollack et al., [*Science*, 234, 1570 (1987)] who reported accelerated hydrolyric rates for Fab fragments were the same as those of the native immunoglobulin. Inasmuch as the antibodies from which paratope-containing portions are obtained are described as raised against or induced by immunogens, paratope-containing (antibody combining site-containing) receptors can also be discussed as being "raised" or "induced" with the understanding that a cleavage step is typically required to obtain an idiotype-containing polyamide from an antibody. Intact antibodies are preferred, however, and are utilized as illustrative of the receptor molecules of this invention.

The receptors useful in the present invention are monoclonal antibodies. A "monoclonal antibody" is a receptor produced by clones of a single cell called a hybridoma that secretes but one kind of receptor molecule. The hybridoma cell is fused from an antibody-producing cell and a myeloma cell or other self-perpetuating cell line.

Techniques for preparing the monoclonal antibodies of the present invention are well known. Such receptors were first described by Kohler and Milsrein, *Nature*, 256, 495 (1975), which is incorporated herein by reference. Monoclonal antibodies are typically obtained from hybridoma tissue cultures or from ascites fluid obtained from mammals into which the hybridoma tissue was introduced. Both methods are described herein.

A "ligand" is defined herein as a molecule that immunoreacts with or binds to a useful receptor molecule antibody combining site. Two types of ligand are contemplated herein. A first is termed an analog ligand and is used as an immunogen (hapten) when bonded to an appropriate immunogenic carrier to induce preparation of receptor molecules and as an inhibitor of the receptor molecule-catalyzed reaction when present without the carrier. The analog ligand is inert to undergoing the catalyzed reaction. The second ligand is referred to as the reactant ligand, substrate ligand, substrate or similar phrase and is a 1-benzyl-1-hydrocarbyl alkene molecule that undergoes the catalyzed epoxidation reaction. The substrate and analog ligands are structurally analogous.

As described herein, chemical analogs of substrate ligands are synthesized that incorporate the quaternary nitrogen atom of a piperidinium compound at a specific, predetermined site relative to the rest of the molecule to mimic the tetrahedral conformation and $sp^3$ character of the transition state in the epoxidation reaction. Further structural features of the analog ligand are discussed hereinafter.

Short polypeptide chains can induce the production of antibodies that recognize and bind to a homologous protein at a predetermined specific site. The present invention carries the earlier work with polypeptides a major step forward. Here, the antibodies (receptors) are induced by an immunizing haptenic first molecule (the analog ligand), and recognize and bind not only to that first molecule, but also to a second, structurally analogous molecule (the substrate reactant ligand).

In binding that second molecule, the receptor catalyzes bond formation in a reaction (which as demonstrated herein is catalytic) of preselected atoms to form an epoxide compound that corresponds in topology to the topology of the immunizing, haptenic first molecule. The correspondence in topology; i.e., size, shape and stereochemistry, provides a means for preselecting the site at which epoxide bond formation in the reacting substrate ligand occurs. Inhibitor ligands that resemble the structure of an analog ligand or a reactant ligand are also bound by receptor molecules and do not undergo a reaction catalyzed by the receptor.

Consequently, by synthesis of a relatively small, immunizing haptenic analog ligand, one can induce the production of receptor molecules that recognize, bind to and catalyze epoxide formation in another molecule that can contain a plurality of alkene (ethylenic unsaturation) groups. Thus, receptor molecules can be prepared that catalyze epoxidation between selected, predetermined carbon atoms of a preselected compound to yield an epoxide product.

The implication of this result is that one can confer the activity of hitherto known or unknown epoxidase (monooxygenase) enzymes to immunoglobulins. Furthermore, the activity of the antibody combining site can be directed to any predetermined site at will by designating the bond to be formed by the piperidinium nitrogen atom placement in the haptenic analog ligand used for immunization.

II. Transition State of Epoxidation and Hapten (Analog Ligand) Design

A process using monoclonal antibody molecules or paratope-containing portions thereof to catalyze the reaction of an ethylenically unsaturated 1-benzyl-1-hydrocarbyl alkene molecule to form an epoxide is contemplated here.

Such a process comprises the steps of (a) admixing the following in an aqueous medium to form a reaction medium:
  (i) an oxidation-effective amount of a peroxycarboximic acid,
  (ii) a catalytically effective amount of monoclonal antibody molecules or paratope-containing portions thereof, and
  (iii) a substrate 1-benzyl-1-hydrocarbyl alkene to which the antibody molecules or paratope-containing portions bind. The substrate bound by the monoclonal antibody molecules or the paratope-containing portions thereof contains up to about 25 carbon atoms bonded to the carbon atoms of the alkenyl (vinyl) double bond including the 1-hydrocarbyl substituent and the phenyl ring of the 1-benzyl substituent. The monoclonal antibodies or paratope-containing portions also bind to an analog of the substrate that is an N-benzyl-N-hydrocarbylpiperidinium compound in which the nitrogen atom of the piperidinium compound analog ligand is analogous to the 1-carbon atom of the alkene substrate. The analog ligand contains no more ring structures bonded to the piperidinium ring than are present in the substrate. The analog ligand also preferably contains up to about 25 atoms in the piperidinium ring and any substituents bonded thereto, exclusive of any substituent used for linking the analog ligand to an immunogenic carrier.

(b) The reaction mixture is maintained under biological reaction conditions for a time period sufficient for the alkene moiety of the substrate to be converted to an epoxide. Inasmuch as only the vinyl group undergoes a change in this reaction, the product otherwise corresponds in structure to the substrate and is referred to as a corresponding epoxide.

Design of the analog ligand flows backward from the structure of the product to be formed through the transition state for bond formation to be mimicked, to the substrate and then to the analog ligand. The general reaction type of interest here will be discussed below, followed by a brief discussion of the products, and then more detailed discussions of the substrate and analog ligands to which a monoclonal catalytic molecule binds, as the structures of the substrate and analog ligands to which the catalyst binds define the catalyst used in the process.

The reaction contemplated here is the antibody paratope-catalyzed oxidation of a particularly substituted olefin (alkene or vinyl group) to form the corresponding epoxide. The contemplated corresponding epoxide products can be as simple as monocyclic compounds such as phenyl propylene oxide derivatives (Compounds 11–14 through phenyl cyclic derivatives (Compound 5).

The corresponding epoxide product formed depends mostly upon the substrate molecule that must include an alkene group bonded to a benzyl group. The carbon of the alkene bonded to the benzyl methylene is also bonded to a hydrocarbyl group such as methyl or a longer alkyl or alkenyl group as is discussed below. These substrate molecules are referred to as 1-benzyl-1-hydrocarbyl alkenes to emphasize the required bonding. More formal names for several substrates and products are also provided hereinafter.

Compounds 6, 10 and 15, below, illustrate the structural requirements for a contemplated substrate, where Ar is a 4-(N-hydroxyethyl)benzamido group that is illustrative of the phenyl group portion of a benzyl group. Thus, Compound 6 that possesses the above-noted structural requirements, is a substrate in a contemplated process. Compound 10 that lacks a hydrocarbyl substituent on the vinyl (alkene) carbon bonded to the benzyl group derivative (the 1-carbon) does not react to form an epoxide. Compound 15, a compound in which one carbon of the double bond is linked directly to the aromatic ring also does not react.

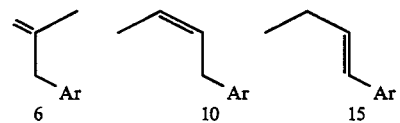

It is also to be understood that the analog ligand that induces the catalytic antibody and that catalyst itself play major roles in the reaction. However, unless the benzyl group and hydrocarbyl substituent are arrayed properly as to the alkene double bond, a desired epoxide does not form.

More specifically, a substrate molecule to which a catalytic antibody binds and that undergoes an epoxide-forming reaction here has a hydrocarbon chain that contains ethylenic unsaturation (a carbon-to-carbon double bond, vinyl group or alkene group) to one carbon atom of which at least (i) a benzyl or substituted benzyl group and (ii) a hydrocarbyl group are bonded. The vinyl group and its two required substituents can be anywhere in that hydrocarbon chain. However, the one carbon atom of the double bond having the two substituent groups (i) and (ii), above, is assigned the 1-position to emphasize the relation of the double bond to the required two substituents and so that the position of the double bond can be unambiguously assigned.

A contemplated substrate can contain a minimum of 10 carbon atoms as in Compound 6 up to a total of about 25 carbon atoms, including the phenyl ring of the recited benzyl substituent. Additional carbon or other atoms bonded to the benzyl group phenyl ring are not included in this calculation. The 15 carbon atoms in excess of the minimum number can be bonded to the other carbon atom of the vinyl group or to the 1-position hydrocarbyl substituent. Alternatively, some or all of those 15 carbon atoms can be part of a ring structure that includes the required vinyl group in the ring as is illustrated by Compound 4, shown hereinafter.

A preferred substrate molecule has a structure corresponding to that of Formula A, below,

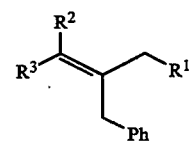

in which Ph is phenyl;
$R^1$, $R^2$ and $R^3$ are each independently hydrogen or hydrocarbyl, or $R^1$ and $R^2$ together with their intervening atoms and vinyl group form a monocyclic, bicyclic or tricyclic ring structure, and the substrate contains a total of up to about 25 carbon atoms bonded to the carbon atoms of the alkene double bond, including the atoms of the depicted phenyl ring.

Compounds in which one of $R^2$ and $R^3$ is other than hydrogen react more rapidly than do those in which both $R^2$ and $R^3$ are hydrogen. Compounds in which both $R^2$ and $R^3$ are other than hydrogen react more rapidly than do compounds in which only one of $R^2$ and $R^3$ is other than hydrogen.

Exemplary non-hydrogen $R^1$, $R^2$ and $R^3$ hydrocarbyl substituent groups include $C_1$-$C_{16}$ alkyl groups such as acyclic methyl, ethyl, isopropyl, hexyl, 2-methylhexyl, octyl, decyl, dodecyl, tetradecyl and hexadecyl, as well as cyclic substituents such as cyclopentane, cyclohexane, cycloheptane, and cyclooctane, as well as their alkyl substituents. An $R^1$, $R^2$ or $R^3$ group can also contain further ethylenic unsaturation so that an above-discussed $C_1$-$C_{16}$ acyclic alkyl or cyclic alkyl group can be present as its corresponding acyclic or cyclic alkenyl substituent such as a but-2-enyl, dodec-2-en-1-yl or cyclohex-3-en-1-yl substituent.

$R^1$ and $R^2$ can also together with their interveningly-bonded carbon atoms form a mono-, di- or tricyclic ring. Exemplary of such monocyclic rings are cyclohexenyl and cyclopentenyl derivatives, whereas an octahydronaphthalenyl derivative exemplifies a bicyclic ring and a dodecahydrophenanthrenyl derivative exemplifes a tricyclic ring.

Again, the sum of the carbon atoms present in the substrate, including the phenyl ring of the benzyl substituent, is about 25, plus two for the vinyl group. The basis for this size limitation stems from the size of an antibody paratope or combining site.

The phenyl ring of the benzyl group that is present in a substrate and in an analog ligand can be substituted or unsubstituted. A substituted phenyl ring is used illustratively here and is shown as Ar. The substituent of an illustative Ar group is a 4-N-(hydroxyethyl)carboxamido group. Other contemplated substituent groups include halo (fluoro, chloro, bromo and iodo), nitro, carboxyl, $C_1$-$C_6$ alkyl carboxylate ($-CO_2$-$C_1$-$C_6$ alkyl), carboxamido ($-CONH_2$), N-mono-$C_1$-$C_6$ alkyl carboxamido ($-CONH$-$C_1$-$C_6$ alkyl), N, N-di-$C_1$-$C_6$ alkyl carboxamido [$-CON(C_1$-$C_6$ alkyl $)_2$] and N, N-di-(hydroxyethyl)carboxamido groups. The number of atoms present as a phenyl ring substituent group is not counted in the above 25 atoms.

An antibody combining site (paratope or binding pocket) is usually reported to be able to accommodate about 5–7 amino acid residues. A seven residue chain includes a chain of about 25 atoms including the N-terminal amino group ($-NH_2$) and C-terminal carboxyl group ($-OH$). Side chains must also be accommodated within the paratope.

That paratopic size is also about the size of a squalene oxide molecule (30 carbons) from which the steroid lanosterol is formed. In addition, Arevalo et al., Nature, 365:859–863 (1993) recently reported that the combining site of a non-catalytic monoclonal anti-progesterone antibody Fab' fragment designated DB3 could accommodate 81–91 percent of each of five steroidal molecules. That paper also noted that the steroidal D ring was embedded in a hydrophobic cavity at the bottom of the binding pocket of that paratope.

Extending the induced fit model for antibody binding to a steroid-epoxide-forming reaction, the size of the substrate here is limited so that substantially all of the substrate; i.e., 80–100 percent, and particularly the epoxide ring-forming portion, can be within the catalytic paratope. Thus, the entire required 1-benzyl group and all of the substituents that can be present need not be bound. Such a size limitation can thereby utilize the binding energy of the antibody-substrate binding interaction to overcome otherwise contrary entropic and/or enthalpic effects present when forming an epoxide.

A hapten structurally analogous to a substrate is utilized to induce the production of catalytic antibodies. That hapten is referred to herein as an analog ligand, analog of the substrate or analog, and in inducing production of a catalyst molecule, the catalytic paratope also immunoreacts with (binds to) the analog ligand.

As noted elsewhere, an analog ligand approximates an unisolatable transition state in the epoxidation reaction. A concerted mechanism has been proposed for peracid epoxidation [Bartlett, Rec. Chem. Prog., 18:111 (1957)] so that charged species should be absent from the transition state. Nonetheless, an analog ligand bearing a formal positive charge has been used here and is presently preferred.

The hapten molecules and induced receptor molecules useful in a present process were originally designed for and successfully used in a process for hydrolyzing a glycosidic bond, a reaction involving a charged transition state. Reymond et al., Angew. Chem. Ing. Ed. Engl., 30(12):1711–1713 (1991). Those haptens and their same receptors were also shown to be useful in catalyzing the hydrolysis of enol ether compounds, a reaction found to involve both an ionizable amino acid residue side chain of the receptor molecule and a hydrophobic interaction between the one or more receptor side chains and the homobenzyl carbon atom of the substrate that undergoes rehybridization from $sp^2$ to $sp^3$. [Reymond et al., J. Am. Chem. Soc., 114:2257–2258 (1992); Ibid., 115:3909–3917 (1993)].

It was therefore surprising that a reaction of a contemplated process that is not believed to include an ionically charged transition state, but might gain some stabilization via a hydrophobic interaction at the homobenzylic carbon atom could obtain enough stabilization to exhibit a catalytic rate enhancement. Another surprising aspect of the present use of catalytic receptor molecules that were also useful in other reactions is that the receptor molecule-catalyzed enol hydrolysis reaction did not require disubstitution at one carbon of the double bond as is required here, and the enolic double bond could be one carbon further removed from the required phenyl ring than is found here. Another surprising aspect here was that the prior reactions catalyzed by these receptors involved a substrate and proton, whereas a molecule much larger than a proton, a peroxycarboximic acid must also interact with the bound substrate here.

A useful haptenic analog ligand is a piperdinium compound whose nitrogen atom is bonded to a benzyl group and also to another hydrocarbyl group, thereby making that quaternary nitrogen atom structurally analogous to the 1-carbon atom of the substrate vinyl group; i.e., the substrate carbon atom to which both the required benzyl and hydrocarbyl groups are bonded. The analog ligand contains no more ring structures than does the substrate, and also contains saturated bonds at the position where the to-be-epoxidized substrate vinyl group is located. Identity of single or multiple bonds in other locations in the hapten and substrate are thought to be of little importance. The hydrocarbyl group bonded to the piperidinium nitrogen atom is preferably the same as that bonded to the substrate 1-position carbon atom along with the benzyl group, but both need not be the same.

Although not wishing to be bound by theory, it is believed that the tetrahedral arrangement of atoms and bonds about the quaternary nitrogen atom coupled with the $sp^3$ hybridization of the piperidinium ring bonds and spacial arrangement of the benzyl and hydrocarbyl groups bonded to that tetrahedrally bonded atom induces a paratope with the appropriate steric and hydrophobic interactions with the substrate to be a catalyst. It is also possible that presence of the positive charge in the hapten induces a charged residue in the receptor providing a hydrophilic region that permits the oxidant to properly approach the double bond to be oxidized or causes the double bond to be near the surface of the paratope where it can be approached by the oxidant.

The analog ligand requirement (a) for a piperidinium ring with its $sp^3$ hybridization as compared to a pyridinium ring having $sp^2$ hybridization, (b) an N-benzyl group, (c) the presence of a hydrocarbyl group on the piperidinium nitrogen instead of a proton, and (d) the presence of no more ring structures than are present in the substrate stem from the fact that a total of 55 monoclonal antibodies were induced by and bound appropriately to haptens of Formulas B, C and D, below, and not one of those paratope-containing molecules exhibited catalytic activity. On the other hand, a total of 9 out of 22 monoclonal antibodies against hapten analog ligand Compound 1, below, and 6 out of 20 monoclonals against hapten analog ligand 2, below, exhibited a rate enhancement for epoxide formation over background. Compounds 1 and 2 have the required structural features, whereas haptens B C and D do not fit those structural requirements as is discussed hereinafter.

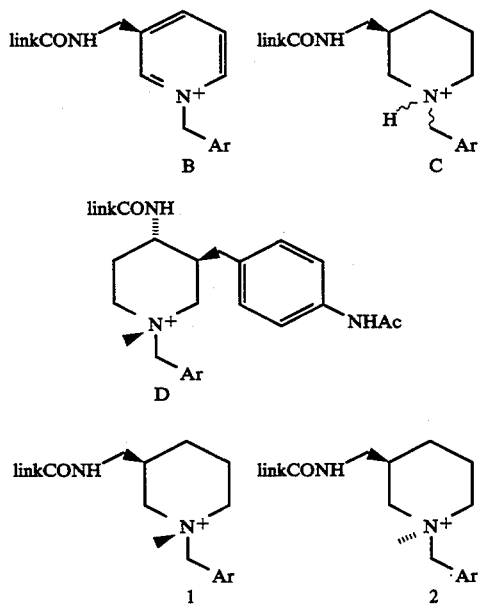

In the above formulas and other formulas herein, "Ar" is a 4-(N-hydroxyethyl)benzamido group, "link" is a linker that bonds the analog ligand to an immunogenic carrier molecule or other molecule, and "Ac" is acetyl.

It is thus thought that hapten B failed to induce catalytic antibodies because all of its ring bonds are hybridized $sp^2$ rather than $sp^3$. Similarly, the protonated rather than alkylated piperidinium hapten C contains a nitrogen atom whose configuration is not locked and that protonation might be lost upon immunization in vivo. It is further thought that the size of hapten D induces a paratope that is too large relative to the size of the substrate for appropriate binding and stabilization.

As a hapten, the analog ligand is not itself immunogenic and must be linked to an immunogenic carrier molecule, usually a protein, to induce the production of antibodies. Depending mostly upon ease of synthesis, the hapten typically is prepared to contain an amine, aminomethyl, carboxyl or hydroxyl group that can be coupled to the linker, and that together with the linker is denoted Z. Although the linker is not a structural feature of the haptenic analog ligand that must be mimicked in the substrate, such mimicking can take place.

It is preferred that the linker be bonded to the carrier molecule via a carboxyl group of the linker. As a consequence, where the hapten contains a carboxyl group for bonding to the linker, —Z, after reaction preferably has the formula —$C(O)NH(CH_2)_nCO_2H$, where n is an integer from 1 to about 9 to provide linkers such as glycine, $\beta$-alanine, 6-aminocaproic acid and 10-aminodecanoic acid. Where the hapten contains an amine, aminomethyl or hydroxyl group for bonding to the linker is preferably a $C_4$-$C_6$ straight chain dicarboxylic acid such as glutaric acid, succinic acid, maleic acid, fumaric acid or adipic acid so that —Z as an amide corresponds to the formula —$NHC(O)(CH_2)_mCO_2H$, where m is an integer that is 2–4, or —$NHC(O)(CH_2)_pCH=CH(CH_2)_qCO_2H$ where p and q are independently zero or one. Ester —Z groups have similar structures with an —O— replacing —NH—, whereas an aminomethyl-containing Z group includes a —$CH_2NH$— in place of the —NH— group.

The structure of a preferred analog ligand molecule corresponds to Formula E, below,

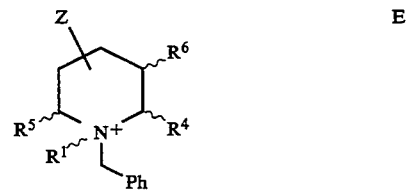

where Ph is phenyl;

$R^1$ is a hydrocarbyl that is the same as $R^1$ in a substrate molecule;

$R^4$, $R^5$ and $R^6$ are independently hydrogen or hydrocarbyl groups or $R^4$ and $R^6$ together form a mono-, bi- or tricyclic ring structure such that the sum of the carbon atoms in $R^1$, $R^4$, $R^5$ and $R^6$ and the depicted benzyl group and the atoms of the depicted piperidinium ring, exclusive of Z, is up to about 30; and Z is a carboxyl-terminated linking group for bonding the analog ligand to an immunogenic carrier that is amide-, amidomethyl- or ester-linked to the analog ligand at a piperidinium ring position between $R^5$ and $R^6$.

The bonds to $R^1$, $R^4$, $R^5$ and $R^6$ are shown as wavy lines to indicate that both stereochemistries are implied. The number of atoms in the analog thus includes the entire piperidinium ring, whereas the 25 carbons of the substrate excludes the vinyl carbons. The substrate and analog can be substantially the same size when those differences in counting are noted.

In accordance with a hapten of Formula E, haptenic analog ligand Compounds 1 and 2 used illustratively herein have structures that correspond to Formula X, below.

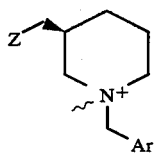

It is thus seen that an analog ligand mimics much of the structure, bonding and size of the substrate and product except for the double bond and epoxide present in the substrate (reactant ligand) and product, respectively, and the presence of a charged nitrogen atom in the analog ligand.

Exemplary substrates, analog ligands and epoxide products are shown in Table 1, below. As can be seen, substrate ligand Compounds 4 and 6-9 were all converted to their respective product Compounds 5 and 11-14, by catalytic receptor molecules raised to the same analog ligand, Compound 1, and each reaction was catalyzed by the same catalyst molecules, antibody 20B11.

TABLE 1

| Substrate[1] | Analog[1,2] | Product[1] |
|---|---|---|
| (cyclopentenyl-CH₂-Ar) 4 | (piperidinyl with linkCONH, N+, CH₂-Ar) 1 | (epoxide on cyclopentane-CH₂-Ar) 5 |
| (CH₂=C(CH₃)-CH₂-Ar) 6 | 1 | (epoxide-CH₂-Ar) 11 |
| (CH₃CH=C(CH₃)-CH₂-Ar) 7 | 1 | (epoxide-CH₂-Ar) 12 |
| (CH₂=C(Et)-CH₂-Ar) 8 | 1 | (epoxide-CH₂-Ar) 13 |
| ((CH₃)₂C=C(CH₃)-CH₂-Ar) 9 | 1 | (epoxide-CH₂-Ar) 14 |
| (cyclohexenyl-CH₂-Ph) I | 1 | (epoxide on cyclohexane-CH₂-Ph) II |
| (octahydronaphthalenyl-CH₂-Ph) III | (decahydroquinoline with linkCONH, N+, CH₂-Ph) IV | (epoxide on decalin-CH₂-Ph) V |

[1]Ar = 4-(N-hydroxyethyl)benzamido; Ph = phenyl.
[2]Link CONH = a linker group amide-bonded to the analog ligand by a reacted aminomethyl group.

Contemplated catalytic monoclonal antibody molecules or their paratope-containing portions bind to a before-defined substrate and analog ligand, and in the presence of an oxidation-effective amount of a peroxycarboximide catalyze the epoxidation of the substrate to form a corresponding epoxide. Contemplated monoclonal catalyst molecules preferably bind to a substrate that corresponds in structure to Formula A, above, and to an analog of the substrate having a structure that corresponds to Formula E, above.

As should be apparent from Table 1 and the results discussed hereinafter, the substrate ligand and analog ligand do not have to be isostructural for catalytic receptors raised to the latter to bind to and catalyze a reaction in the former. Rather, such structural similarity helps to assure binding of both and reaction of the substrate. A $K_M$ value of between about 10 mM and 500 nM between substrate and catalyst is preferred. A $K_M$ value in the above range can also illustrate analogy between a substrate and analog.

The present catalyzed epoxidation reaction are stereoselective; i.e., a cis olefin provides a cis epoxide and a trans olefin provides a transepoxide. More surprisingly, a contemplated catalyzed reaction is also enantioselective; one enantiomer is formed in excess or to the exclusion of the other enantiomer.

Thus, when epoxidized free in solution with the same peroxycarboximic acid, a contemplated substrate forms racemic epoxides. Here, in the monoclonal receptor-catalyzed reaction, one enantiomer is formed in a greater amount than the other. Examples of bulk optical purity (optical purity of the catalyzed and uncatalyzed reaction products) are provided hereinafter, as are enantiomeric excesses (ee) for the catalyzed epoxidation. As will be seen in Table 2 hereinafter, enantioselection was substantially complete for substrate Compounds 4 and 8.

Exemplary substrate syntheses are discussed hereinafter in the examples. Other useful substrates can be prepared using analogous reactions. Syntheses of the haptenic analog ligands used here as illustrative, Compounds 1 and 2, were described in Reymond et al., *Angew. Chem. Int. Ed. Engl.*, 30(12):1711–1713 (1991). Thus, a 1:1 mixture of diastereomeric haptens was produced starting with N-methyl-3-hydroxymethylpiperidine and 4-(chloromethyl)-N-(2'-hydroxyethyl)benzamide. Those diastereomers were separated by reverse phase high performance liquid chromatography. Similar analog ligands such as Compound IV can be prepared by analogous procedures.

A peroxycarboximic acid is the oxidant whose oxidation of the double bond is catalyzed by a receptor molecule. A peroxycarboximic acid is itself the in situ-formed reaction product of base-catalyzed addition of hydrogen peroxide to an appropriate nitrile such as a $C_1$-$C_3$ nitrile like acetonitrile, propionitrile, butyronitrile and isobutyronitrile. Use of other water-soluble nitriles such as 4-cyanobenzoic acid is also contemplated. Acetonitrile is the preferred nitrile, with acetoperoxycarboximic acid being the preferred oxidant.

It was also quite surprising that the protein catalyst could survive contact with this oxidant, even though it is a relatively mild oxidant. Thus, after 24 hours of reaction at room temperature and an average of more than three catalytic turnovers, the catalyst molecules maintained their original activity. Even after 48 hours, no decrease in catalysis was observed.

The peroxycarboximic acid is present in the reaction mixture in an oxidation-effective amount. That amount is an amount effective for converting substrate into product epoxide via the catalyst.

As is noted elsewhere, formation of the peroxycarboximic acid from hydrogen peroxide and an appropriate nitrile is the slow, rate-controlling, step in this process. The concentration of peroxycarboximic acid is therefore most easily determined by the initial amounts of hydrogen peroxide and nitrile present in the reaction mixtures.

Each of hydrogen peroxide and the selected nitrile can be present at up to about 10 percent by volume of the reaction mixture, with a volume percentage of up to about 5 percent for each being preferred. It is still more preferred that each of the hydrogen peroxide and nitrile peroxycarboximic acid-forming reactants be present at about 0.5 to about 3 volume percent of the reaction mixture. Additional exemplary amounts of hydrogen peroxide and acetonitrile, the preferred nitrile starting material are provided hereinafter.

A contemplated monoclonal paratope-containing molecule (receptor) can be referred to as being biologically active. Biological activity of a receptor molecule is evidenced by the binding of the receptor to its antigenic reactant ligand, inhibitor ligand or analog ligand upon their admixture in an aqueous medium, at least at physiological pH values and ionic strengths. Preferably, the receptors also bind to an antigenic ligand within a pH value range of about 5 to 9, and at ionic strengths such as that of distilled water to that of about one molar sodium chloride.

The substrate ligand, receptor catalyst molecules and peroxycarboximic acid are admixed in an aqueous medium. That medium is typically buffered between pH values of about 5 to about 9 and contains salts such as phosphate and sulfate at appropriate concentrations to preserve protein structure, as is well known. Chloride salts as are often present in biological systems are not generally used in a contemplated process to avoid chlorhydrine formation.

A contemplated aqueous medium can also contain up to about 10, and more preferably about 1 to about 5, volume percent of a water-miscible organic solvent that does not itself react with the hydrogen peroxide or peroxycarboximic acid, nor denature the protein catalyst. Exemplary solvents include methanol, ethanol and isopropanol. Acetonitrile that is reactive here can also be used and is particularly preferred as it functions not only as a solvent but also as a source of the peroxycarboximic acid.

Use of a two-phase aqueous/water-immiscible organic solvent reaction medium as was utilized in Janda et al., *Science*, 259:490–493 (1993), citation 22, is also contemplated. See, also Ashley et al., *J. Org. Chem.*, 57:6691–6693 (1992), and the citations therein. That biphasic medium included 5 volume percent of a buffered aqueous solution and 95 volume percent hexane.

The aqueous medium typically has a pH value of about 5 to about 9, and preferably about pH 6.0 to about 8.0. pH Values greater and less than those recited values can also be utilized so long as the catalyzed reaction is not substantially interfered with or inhibited.

The catalytic reactions are typically carried out at ambient room temperature; i.e., at about 20° to about 25° C., or at 37° C., and at an ambient atmospheric pressure; i.e., at about one atmosphere. However, temperatures down to about the freezing point of the aqueous medium and up to about the boiling point of the medium at atmospheric pressure can also be used. As is known, proteins such as the receptor molecule tend to denature at elevated temperatures such as those at which an aqueous medium boils, e.g., at about 100° C. and thus temperatures below about 40° C. are preferred. As is also well known, reactions that follow multimolecular kinetic expressions decrease in rate as the temperature decreases. Thus, a minimal temperature of about 15° C. is preferred.

The biological reaction conditions are the temperature, pH value and presence of salts discussed above and in regard to a receptor molecule being biologically active.

The reactant ligand (substrate) is present in a reaction mixture in an amount up to its solubility in the aqueous medium. Normally used concentrations of the reactant ligand (substrate) are about 0.1 micromolar ($\mu$M) to about 10 millimolar (mM), with that amount also being a function of the solubility of the reactant ligand in the solvent medium. Where the product is desired, per se, relatively higher concentrations are used as compared to lower concentrations where a reaction mechanism or reaction kinetics are to be studied.

An effective amount of the catalytic receptor molecule is also present. That effective amount is typically a catalytic amount; i.e., the receptor is used at a molar ratio to the reactant ligand of about 1:2 to about 1:10,000, with a molar ratio of about 1:10 to about 1:100 being preferred. The ratio of receptor molecule to reactant ligand typically depends upon the specific activity of the receptor molecule toward the reactant ligand and the purpose of the user in running the reaction.

Thus, where the product is desired, a relatively higher concentration of receptor and higher receptor to reactant ligand ratio are used. Where the reaction mechanism or kinetics of the reaction are being studied, a lower concentration and ratio are typically used. A stoichiometric amount of receptor or more can also be used, but since the receptor is a catalytic molecule, use of even a stoichiometric amount can be wasteful. Thus, at least a catalytic amount of the receptor is utilized.

The admixture formed by admixing reactant ligand molecules, peroxycarboximic acid and receptor molecules in an aqueous medium is maintained for a time period sufficient for the binding and reaction to occur. The duration of that maintenance period is a function of several parameters including the receptor and reactant ligand selected, their concentrations, pH value, and temperature, as well as what is being sought from the reaction.

Thus, where kinetic studies are being carried out, maintenance times of minutes to hours are frequently used. Where the reaction products are desired, maintenance times of hours to days are more usual.

The epoxide produced in a contemplated reaction is preferably recovered. Such recovery is not, however, required, as where a corresponding gem-diol is formed in situ from the product by acid or base catalyzed opening of the epoxide ring. Any excess oxidant is typically destroyed prior to effecting epoxide ring opening.

A formed epoxide product can be easily recovered. Thus, after destroying any residual peroxycarboximic acid and hydrogen peroxide as with peroxidase, the reaction medium is typically concentrated, and any organic solvent present is removed from the aqueous medium. The desired product can then be recovered using chromatographic techniques described herein. It can also be useful to extract the product with a water-immiscible organic solvent such as dichloromethane, benzene or ethyl acetate prior to chromatographic separation.

III. Results

It was recently reported [Reymond et al., *J. Am. Chem. Soc.*, 114:2257 (1992); and Reymond et al., *J. Am. Chem. Soc.*, 115:3909 (1993)] that antibodies raised against haptenic Compounds 1 and 2 catalyze the hydrolysis of enol ethers such as Compound 3 to form optically pure carbonyl compounds.

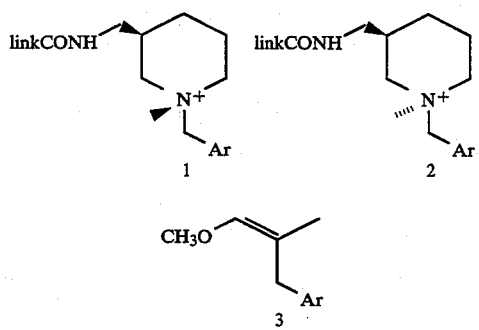

In the case of antibody 14D9 (anti-1) and enol ether Compound 3, it was shown that antibody catalysis originated in two effects of comparable magnitude: (1) general acid catalysis by a carboxyl group and (2) pyramidalization of the enol ether's $\beta$-carbon by hydrophobic contacts. It was reasoned that the second effect might also activate alkenes analogous to Compound 3 towards epoxidation, as the reaction involves rehybridization from $sp^2$ to $sp^3$ at the homobenzylic carbon. It was also reasoned that some members of the antibody series against haptenic Compound 1 might catalyze the epoxidation of alkenes if an appropriate reagent for providing oxygen from solution could be found.

Alkene Compounds 4 and 6 through 10 were prepared according to known procedures [Negishi et al., *Tetrahebron Lett.*, 22:2715 (1981)]. Reference epoxides were obtained by oxidation of the olefins with m-chloroperbenzoic acid ($CH_2Cl_2$, solid $NaHCO_3$ added) and purified by preparative HPLC. X-ray structure of epoxide 12 allowed the assignment of stereochemistry of Compounds 7 and 8.

The oxygen donor of choice had to be compatible with the antibody and its aqueous environment. This proved to be a major challenge. Several possible reagents were surveyed: [magnesium monoperphthalate, resulting in rapid cleavage of the antibody; manganese (III) tetrakis(4-carboxyphenyl)porphine with hydrogen peroxide, leading to destruction of the cofactor itself; and iron(III) tetrakis(pentafluorophenyl)porphine that was insoluble in water. See, generally: Brougham et al., *Synthesis*, 1015 (1987); and Harriman et al., *J. Chem. Soc., Faraday Trans. II*, 75:1532 (1979)].

It was found that the combination of hydrogen peroxide and acetonitrile in aqueous buffer under neutral conditions effected clean epoxidation of the contemplated substrates without affecting the antibody itself. [Payne et al., *J. Org. Chem.*, 26:659 (1961); Payne, *Tetrahedron*, 18:763 (1962); Bach et al., *Org. Chem.*, 60:80 (1981); Arias et al., *J. Org. Chem.*, 48:888 (1983). The use of chiral cyanoformates induces up to 20 percent ee: Masaki et al., *Chem. Lett.*, 1937 (1991).] The species that delivers oxygen to the alkene is a peroxycarboximidic acid formed by base catalyzed addition of hydrogen peroxide to the nitrile. [MacIsaac et al., *J. Org. Chem.*, 36:3048 (1971).]

Although peracid formation is rate limiting, the alkene epoxidation step is kinetically observable due to the competing destruction of the peracid with $H_2O_2$ to form singlet oxygen and acetamide [Wiberg, *J. Am. Chem. Soc.*, 75:3961 (1953); Wiberg, *J. Am. Chem. Soc.*, 77:2519 (1955); and McKeown et al., *Nature*, 203:1063 (1964)]. This dead cycle with $H_2O_2$ holds the active peracid species at a very low concentration and might explain the mildness of this reagent towards the antibody. The uncatalyzed reaction is directly proportional to both the alkene (20 to 500 $\mu$M) and the acetonitrile concentration (5 to 383 mM). Measurements here were made in 50 mM phosphate buffer, 50 mM sulfate, at pH 6.56 and 725 mM $H_2O_2$.

There was no decrease in catalysis when the antibody-catalyzed epoxidation was followed over a period of 48 hours using the assay conditions described below. The reactivity of the alkenes under these conditions increases with carbon substitution 6<7≈8<9 [Carlson et al., *J. Org. Chem.*, 36:3832 (1971); and Swern, *J. Am. Chem. Soc.*, 69:1692 (1947)].

Using Compounds 6 to 9, 4 and 15 as test olefins, an extensive survey for possible catalysts was conducted. For catalysis of epoxide formation, 22 antibodies against haptenic analog 1 and 20 antibodies against haptenic analog 2 were assayed. Assay conditions: 50 mM phosphate, pH 6.56, 50 mM $Na_2SO_4$, ambient room temperature. Sulfate replaces chloride to avoid chlorohydrine formation. The ionic strength is required to preserve the antibody structure: [alkene]=250 $\mu$M, [antibody]=1.5 to 1.8 mg/mL, [$H_2O_2$]=725 mM, [$CH_3CH$=96 to 287 mM. In each case, epoxide formation was followed by reversed-phase HPLC (Vydac 218TP54, 0.46 cm $\phi \times 25$ cm, flow 1.5 mL/min, eluent: 20–25 percent $CH_3CN$ in $H_2O$, 0.1 percent trifluoracetic acid; UV-detection ($\lambda$=240 nm)) using an internal standard (N-ethylbenzamide for Compound 6–8, and 15, N-propyl-o-toluoylamide for Compounds 4 and 9).

Nine anti-1 antibodies and six anti-2 antibodies showed rate enhancements of epoxide formation over background for either Compound 6 (6 anti-1 and 2 anti-2), Compound 7 (4 anti-1 and 4 anti-2), Compound 8 (4 anti-1 and 1 anti-2) or Compound 4 (2 anti-1, no anti-2). The antibody catalysis was quantitatively inhibited by addition of hapten, thereby showing that the reaction took place in the antibody combining site. In these samples the reaction rate ($k_{uncat}$, Table 2, below) was in accordance to the measured background rate with antibody-free samples.

One antibody (20B11, anti-1) was characterized in detail. This antibody catalyzed the epoxidation of Compounds 4, and 6–9 (Table 2), following Michaelis-Menten kinetics. As noted before, no catalytic activity was detected with Compounds 10 and 15, suggesting that proper placement of the double bond as well as double substitution at the homobenzylic carbon are essential for catalysis. Kinetic data for acetonitrile were collected using substrate Compound 7 (200 $\mu$M), giving an apparent $K_M$=180 mM and $k_{cat}$=1.7×10$^{-4}$ s$^{-1}$ for 725 mM $H_2O_2$ at pH 6.56.

TABLE 2

| Kinetic data obtained for different alkenes with antibody 20B11 | | | | | |
|---|---|---|---|---|---|
| Alkene | $K_M$ ($\mu$M) | $k_{cat}$ (s$^{-1}$) | $k_{uncat}$ (s$^{-1}$) | $k_{cat}/k_{uncat}$ | ee (%)$^a$ |
| 6 | 260 | 1.4 × 10$^{-5}$ | 2.4 × 10$^{-7}$ | 60 | — |
| 7 | 120 | 6.4 × 10$^{-5}$ | 5.2 × 10$^{-7}$ | 125 | 67 |
| 8 | 140 | 3.0 × 10$^{-5}$ | 5.9 × 10$^{-7}$ | 50 | >98 |
| 4 | 85 | 5.0 × 10$^{-5}$ | 1.1 × 10$^{-6}$ | 40 | >98 |
| 9 | 60 | 3.6 × 10$^{-5}$ | 2.9 × 10$^{-6}$ | 15 | — |

$^a$Analysis on chiral phase HPLC (Chiracel OD ™). The numbers correspond to product formed by catalytic antibodies. The analyzed samples contain approximately 30% of racemic product formed by the uncatalyzed reaction. The optical purity for the bulk product were 47, 64, and 71% ee for Compounds 7, 8, and 4, respectively. The absolute configuration of the epoxides was not determined.

The enantioselectivity of the antibody-catalyzed epoxidation was investigated for three substrates as follows: samples of 380 $\mu$L were prepared, containing the highly purified antibody (23 $\mu$M), the alkene Compound 7 (or Compounds 8 or 4 at 250 $\mu$M), acetonitrile (287 mM) and $H_2O_2$ (725 mM) in 50 mM phosphate buffer, 50 mM sulfate, pH 6.56. Two aliquots of 15 $\mu$L were taken out. One was mixed with 1 $\mu$L of a 8.3 mM solution of inhibitor to provide a final concentration of 250 $\mu$M, with the other being left uninhibited. After incubation overnight (about 18 hours), epoxide formation had reached 31.8 percent (or 30.7 percent, or 32.5 percent, respectively) in the catalyzed sample and 9.4 percent (10.9 percent, or 9.0 percent, respectively) in the inhibited sample for Compounds 7, 8 and 4. At that stage, the antibody had carried out, on average, 3.5 turnovers per active site and still showed the full catalytic activity. The remaining about 350 $\mu$L (380 $\mu$L–2X15 $\mu$L) of catalyzed reaction mixtures provided sources for the epoxide products 12, 13, and 5, which were isolated by reverse phase HPLC and analyzed on a chiral HPLC column [Daniel Chiralcel ™ OD HPLC-column) 0.046 cm $\phi \times 25$ cm, 70 percent hexane, 30 percent isopropanol, flow 1.0 mL/min; UV-detection ($\lambda$=240 nm)). $t_R$ (12)=13.3 min, 17.2 min; ratio 2.8:1. $t_R$ (13)=15.2 min, 22.3 min; ratio 4.5:1. $t_R$ (5)=10.6 min, 18.8 min; ratio 5.9:1. Compound 11 could not be resolved into the two enantiomers on this and three other chiral HPLC columns. As shown in Table 3, asymmetric induction by the antibody is complete for substrate Compounds 8 and 4. The incomplete induction observed with Compound 7 suggests that this substrate might adopt two reactive conformations within the antibody binding site.

IV. Preparation of Conjugates and Inocula

Conjugates of haptenic analog ligand molecules with antigenic (immunogenic) protein carriers such as keyhole limpet hemocyanin (KLH) can be prepared, for example, by activation of the carrier with a coupling agent such as MBS (m-maleimidobenzoyl-N-hydroxy succinimide ester), and coupling to the thiol group of the analog ligand. See, for example, Liu et at., *Biochem.*, 80, 690 (1979). As is also well known in the art, it is often beneficial to bind a compound to its carrier by means of an intermediate, linking group.

Useful carriers are well known in the art and are generally proteins themselves. Exemplary of such carriers are keyhole limpet hemocyanin (KLH), edestin, thyroglobulin, albumins such as bovine serum albumin or human serum albumin (BSA or HSA, respectively), red blood cells such as sheep erythrocytes (SRBC), tetanus toxoid, cholera toxoid as well as polyamino acids such as poly(D-lysine:D-glutamic acid), and the like.

The choice of carrier is more dependent upon the ultimate intended use of the antigen than upon the determinant portion of the antigen, and is based upon criteria not particularly involved in the present invention. For example, if the conjugate is to be used in laboratory animals, a carrier that does not generate an untoward reaction in the particular animal should be selected.

The carrier-hapten (carrier-analog ligand) conjugate is dissolved or dispersed in an aqueous composition of a physiologically tolerable diluent such as normal saline, PBS, or sterile water to form an inoculum. An adjuvant such as complete or incomplete Freund's adjuvant or alum can also be included in the inoculum. The inoculum is introduced as by injection into the animal used to raise the antibodies in an amount sufficient to induce antibodies, as is well known.

In an exemplary procedure, the linker 5-[(2,5-dioxo-1-pyrrolidinyl)oxy]-5-oxopentanoyl chloride was coupled to the aminomethyl group of a haptenic analog ligand to form Compounds 1 and 2. The reaction was carried out in dimethylformamide at $-30°$ C. in the presence of ethyldiisopropylamine. The resulting hapten was coupled to KLH or BSA to form immunoconjugates. These reactions are also discussed in Reymond et al., *Angew. Chem. Int. Ed. Engl.*, 30(12):1711–1713 (1991), and the citations therein.

V. Preparation of Monoclonal Receptors

The foregoing KLH conjugates (about 100 μg) were used to immunize mice (129G1X* strain), and monoclonal antibodies were obtained as described by Niman et al., *Proc. Natl. Acad. Sci. USA*, 77, 4524 (1980) and Niman et al., in *Monoclonal Antibodies and T-Cell Products*, Katz, D.H. ed., 23–51, CRC Press, Boca Raton, FL (1982). The lymphocytes employed to form the hybridomas of the present invention can be derived from any mammal, such as a primate, rodent (e.g., mouse or rat), rabbit, guinea pig, cow, dog, sheep, pig or the like. As appropriate, the host can be sensitized by injection of the immunogen, in this instance a haptenic analog ligand, followed by a booster injection, and then isolation of the spleen.

It is preferred that the myeloma cell line be from the same species as the lymphocytes. Therefore, fused hybrids such as mouse-mouse hybrids [Shulman et al., *Nature*, 276, 269 (1978)] or rat-rat hybrids [Galfre et al., *Nature*, 277, 131 (1979)] are typically utilized. However, some rat-mouse hybrids have also been successfully used in forming hybridomas [Goding, "Production of Monoclonal Antibodies by Cell Fusion," in *Antibody as a Tool*, Marchalonis et al., eds., John Wiley & Sons Ltd., p. 273 (1982)]. Suitable myeloma lines for use in the present invention include MPC-11 (ATCC CRL 167), P3X63-Ag8.653 (ATCC CRL 1580), Sp2/0-Ag14 (ATCC CRL 1581), P3X63Ag8U.1 (ATCC CRL 1597), Y3-Ag1.2.3. (deposited at Collection Nationals de Cultures de Microorganisms, Paris, France, number I-078) and P3X63Ag8 (ATCC TIB 9). The non-secreting murine myeloma line Sp2/O or Sp2/O-Ag14 is preferred for use in the present invention.

The hybridoma cells that are ultimately produced can be cultured following usual in vitro tissue culture techniques for such cells as are well known. More preferably, the hybridoma cells are cultured in animals using similarly well known techniques with the monoclonal receptors being obtained from the ascites fluid so generated. The animals used for generation of the ascites fluid were female 129G1X* mice bred in the mouse colony of The Scripps Research Institute, La Jolla, Calif.; however, when animals other than mice are used for preparation of the hybridomas, mice or that animal type can be used for the production of ascites fluid.

In particular, an exemplary monoclonal receptor was produced by the standard hybridoma technology of Kohler et al., *Nature*, 256, 495 (1975) and Enguall, E., *Methods Enzymol.*, 70, 419 (1980). Specifically, female 129GIX* mice were immunized by intraperitoneal injection with an inoculum of 100 micrograms of conjugate (e.g., Compound 1 or 2 linked to KLH) mixed with RIBI adjuvant (MPL and TDM emulsion). Two weeks later, the mice were again injected in a like manner with 50 micrograms of the foregoing conjugate in PBS/alum. After an additional four-eight weeks, the mice were immunized intravenously with 50 micrograms of the conjugate. The spleens were removed from the mice, and the spleen cells were fused to myeloma cells.

The spleens cells were pooled and a single cell suspension was made. Nucleated spleen cells (about $1.4 \times 10^8$) were then fused with about $1.4 \times 10^2$ Sp2/0 and about $2.3 \times 10^8$ HL non-secreting myeloma cells in the presence of a cell fusion promoter (polyethylene glycol 2000). A hybridoma that produces a particular monoclonal antibody was selected by seeding the spleen cells in 96-well plates. Each well contains 150 μl Dulbecco's modified Eagle medium (DMEM) plus 2 percent bovine serum albumin (BSA, 1 percent nutridoma) hypoxanthine, aminopterin and thymidine (i.e., HAT medium) which does not support growth of the unfused myeloma cells.

After two to three weeks, the supernatant above the cell clone in each well was sampled and tested by an ELISA assay (enzyme linked immunosorbent assay as described hereafter) for the presence of antibodies against Compound 1 or 2 bound to BSA. Positive wells were cloned twice by limiting dilution. Those clones that continued to produce Compound 1- or 2-specific antibody after two clonings were expanded to produce larger volumes of supernatant fluid. The hybridoma and the monoclonal receptors produced therefrom and described herein are identified by the laboratory designation as discussed herein.

The procedures used here for preparation of the conjugate, immunization and hybridoma formation and screening were those reported by Reymond et al., *Angew. Chem. Int. Ed. Engl.*, 30(11):1711–1713 (1991) and are substantially the same as those reported in Janda et al., *Science*, 259:490–493 (1993).

A monoclonal receptor of the present invention can also be produced by introducing, as by injection, the hybridoma into the peritoneal cavity of a mammal such as a mouse. Preferably, as already noted, syngeneic or semi-syngeneic mammals are used, as in U.S. Pat. No. 4,361,549, the disclosure of which is incorporated herein by reference. The introduction of the hybridoma causes formation of antibody-producing hybridomas after a suitable period of growth, e.g. 1-2 weeks, and results in a high concentration of the receptor being produced that can be recovered from the bloodstream and peritoneal exudate (ascites) of the host mouse.

Although the host mice also have normal receptors in their blood and ascites, the concentration of normal receptors is typically only about five percent that of the monoclonal receptor concentration.

Monoclonal receptors are precipitated from the ascitic fluids, purified by anion exchange chromatography, and dialyzed against three different buffers. The procedures used were as described in Janda et al., *Science*, 259:490–493, except that BisTris buffer was used.

Antibodies obtained are judged to be greater than 95 percent homogeneous by sodium dodecyl sulfate polyacrylamide gel electrophoresis [Laemmli, V. *Nature*, 227:680 (1970)]. The resulting concentrated solutions containing isolated IgG fractions were typically prepared into stock solutions of receptor at 1–20 mg/ml using an appropriate buffer such as 50 mM Tris-HCl, BisTris or sodium phosphate containing 0.01M sodium azide.

A total of 42 monoclonal antibodies were induced (raised) against haptenic Compounds 1 and 2 and were assayed using Compounds 4 and 6–9. The presence, in a reaction mixture of more than one-third of the monoclonal antibodies (15/42; 9 anti-1 and 6 anti-2 antibodies) caused a rate enhancement in epoxide formation over the background in the absence of paratope-containing molecules. The numbers of catalytic molecules for each compound as substrate are shown in Table 3, below.

TABLE 3

| | Catalytic Monoclonals | |
|---|---|---|
| Substrate Compound #[1] | Anti-Compound 1 Hapten[1,2] | Anti-compound 2 Hapten[1,2] |
| 4 | 2 | 0 |
| 6 | 6 | 2 |
| 7 | 4 | 4 |
| 8 | 4 | 1 |

[1]See Table 1 for Compound Structures.
[1]Compound 2 is the diastereomer of Compound 1.

Epoxidation catalyst monoclonal receptors to Compound 1 secreted by one hybridoma were studied more closely than were the others. The hybridoma that produces the catalytic monoclonal receptor, given laboratory designation 20B11, was deposited at the American Type Culture Collection, 12301 Parklawn Drive, Rockville, Md. on Jan. 24, 1994 and was given ATCC accession number HB 11531.

The present deposit was made in compliance with the Budapest Treaty requirements that the duration of the deposit should be for 30 years from the date of deposit or for five years after the last request for the deposit at the depository or for the enforceable life of a U.S. patent that matures from this application, whichever is longer. The hybridoma will be replenished should it become non-viable at the depository.

A Fab fragment of a monoclonal receptor can be prepared from the purified receptor using predigested papain in a 0.1M sodium acetate buffer, at a pH value of 5.5, at 37° C., followed by reaction with iodoacetamide. The Fab fragment is typically further purified by anion exchange chromatography, dialysis, and DEAE anion exchange chromatography, and its homogeneity is judged by gel electrophoresis.

VI. Enzyme-linked Immunosorbent Assay (ELISA)

The binding of an analog ligand by the induced monoclonal receptor molecule was assayed by ELISA with antibody at a fixed concentration in the range of its titer and varying inhibitor (Compound 1) concentration. Use of Compound 1 as inhibitor helps to assure that an observed binding interaction is antigen-specific.

Assays were performed in flat-bottom polyvinyl microtiter plates (Dynatech, Alexandria, Va.). Illustratively, the wells were coated with a solution comprising Compound i bonded to BSA as the antigen ligand in phosphate buffered saline (PBS) using 50 microliters of solution per well. BSA was used as a carrier to bind the hapten to the cell wall, and an analog ligand/BSA conjugate was used in place of the immunizing KLH-containing conjugate to screen out possible anti-KLH antibodies.

The bound ligands were coated at 1 microgram per milliliter. The plates were then incubated overnight at 37° C. in a dry oven. The dried plates were stored at 4° C. until use. Prior to the ELISA assay, dried plates were rehydrated by two washes of two minutes each with ten millimolar (mM) PBS, pH 7.4, containing 0.1 percent polyethylene sorbitan monolaureate (Tween 20) and 0.02 percent Thimerosal (sodium ethylmercurithiosalicylate), (Sigma, St. Louis, Mo.).

In order to reduce non-specific binding, hybridoma supernatants were diluted 1:2 in washing buffer containing 0.1 percent BSA as diluent. Fifty microliters of diluted hybridoma supernatants were thereafter added to each well and incubated for one hour at 4° C. on a gyroshaker to contact the monoclonal antibody-containing supernatant with the bound Compound 1. Following two washes of two minutes each, 50 microliters of peroxidase-labeled goat anti-mouse IgG+IgM (Tago, Burlingame, Calif.), diluted 1:1000, were added to each well, and the reaction mixture was incubated at 4° C. for one hour to bind the labeled antibody to bound monoclonal antibody.

The substrate used to assay bound peroxidase activity was prepared just prior to use and consisted of 400 microgram/ml o-phenylenediamine (Sigma, St. Louis, Mo.) in 80 mM citrate-phosphate buffer, pH 6.0, containing 0.12 percent $H_2O_2$. After two final washes, 50 microliters of substrate solution were added to each well, and color was allowed to develop for 15 minutes in the dark. Color development was stopped by adding 25 microliters of four molar $H_2SO_4$ to each well and the optical density at 492 nanometers (nm) was measured with a Multiskan ELISA plate reader.

For another preparation of the receptor molecules, the gene that encodes an antibody combining site-forming fragment can be obtained from any cell that produces an antibody molecule that immunoreacts as discussed herein. A preferred cell is a hybridoma cell.

For examples of general recombinant DNA cloning methods, see *Molecular Cloning*, Maniatis et al., Cold Spring Harbor Lab., N.Y., 1982; *DNA Cloning*, Glover, ed., IRL Press, McLean Va. (1985). For the genomic cloning and expression of immunoglobulin genes in lymphoid cells, see Neuberger et al., *Nature*, 312:604–8 (1984); Ochi et al., *Proc. Natl. Acad. Sci. USA*, 80:6351–55 (1987); and Oi et al., *Proc. Natl. Acad. Sci. USA*, 80:825–29 (1983). For cloning of immunoglobulin genes from hybridoma cells and expression in *Xenopus* oocytes, see Roberts et al., *Protein Engineering*, 1:59–65 (1986), and see Wood et al. for expression in yeast. *Nature*, 314:446–9 (1985).

Assays for formation of product epoxides were carried out by reversed phase HPLC using a Vydac ™ 2187P54 column.

VII. Best Mode for Carrying Out the Invention General

$^1$H NMR spectra were obtained on a Bruker ™ AM-300 spectrometer, using the chloroform signal as internal reference (7.27 ppm). $^{13}$C NMR spectra were obtained on a Bruker ™ AMX-500 spectrometer, using the chloroform signal as internal reference (77.0 ppm). All mass spectra and HRMS (high resolution mass spectra) are FAB spectra (nitrobenzyl alcohol as matrix) and were provided by the Scripps Research Institute facility (Gary Siuzdak). Combustion analyses and X-ray structure were provided by Raj K. Chadha, Scripps Research Institute.

General procedure for the synthesis of the alkenes via palladium-coupling

Methyl-4(bromomethyl)benzoate (1.15 g, 5.0 mmol) and activated zinc (0.32 g, 5.0 mmol) were stirred for 10 minutes in dry THF (25 mL) under argon until most of the zinc was dissolved. For activation, about 10 g of zinc powder were stirred for five minutes in each solution or solvent as follows: 3N HCl (3 times 40 mL), 40 mL water, 40 mL ethanol, and 40 mL ether. After decanting the ether, the residue was dried under vacuum, stored under argon and usually can be used for several weeks. To the solution of [4-(methoxycarbonyl)benzyl] zinc bromide the vinylic bromide (2 equivalents, 10 mmol) was added and then solid Pd(PPh3)4 (0.40 g, 0.4 mmol). When heated to 60° C., the benzyl zinc bromide was consumed after 15 to 20 minutes. The THF was evaporated and the product isolated by chromatography of the residue on silica gel (hexane/ethyl acetate 90/10 by volume, $R_f \approx 0.35$). The isolated yields of the alkene Compounds 6, 7 and 8 (as a mixture), and 10 were between 80 and 90 percent. Subhash C. Sinha is thanked for the donation of a sample of (4-(methoxycarbonyl)phenyl)-1-cyclopentenylmethane.

Amidation of all substrates was performed by stirring in 2-aminoethanol (about 5 mL for 0.2 g of ester), without additional solvent, for 24 to 48 hours at room temperature. The reaction can be followed by TLC. Heating can effect partial isomerization of the double bond to the styrene.

After diluting with dichloromethane the 2-aminoethanol is removed by extraction with water, the organic layer washed with brine, dried over sodium sulfate and the solvent removed under vacuum. All amides were purified by preparative HPLC on a Waters ™ Prep-PAK 500 reversed phase column (eluent water/acetonitrile). This purification is important to remove all traces of 4-methyl-N-hydroxyethyl benzamide that is formed in small amounts as a sideproduct in the palladium coupling reaction, as the retention time of this simple amide on reversed phase HPLC is similar to the epoxides of interest.

EXAMPLE 1

4-(1'-Cyclopentenylmethyl)-N-hydroxyethyl benzamide (Compound 4)

Obtained by the palladium coupling reaction starting from 1-chlorocyclopentene. Due to the low reactivity of the cyclic chloro compound, the ester contains about 50 mol percent of the reduction product. After conversion to the amide, that reduction product is removed completely during preparative HPLC purification (eluent: water and CH3CN/water (50/50), gradient 80/20 to 20/80 over 60 minutes, flowrate 100 mL/minute). Evaporating the acetonitrile under vacuum and lyophilizing gave pure Compound 4 as a white powder.

$^1$H NMR (300 MHz, CDCl3): $\delta$=7.71, 7.26 (2d, 4H, Ar), 6.56 (bs, 1H, NH), 5.34 (m, 1H, HC=C), 3.85 (t, J=5.0 Hz, 2H, —CH2OH), 3.69–3.63 (m, 2H, —CH2NH), 3.43 (s, 2H, CH2Ar), 2.35–2.29 (m, 2H, CH2 cyclopentene), 2.25–2.13 (m, 2H, CH2 cyclopentene), 1.86 (quintet, J=7.0 Hz, 2H, CH2 cyclopentene). Anal. Calcd for C15H19NO2 (245.3): C, 73.44; H, 7.81; N, 5.71. Found: C, 73.56; H, 7.87; N, 5.83.

EXAMPLE 2

4-(2'-Methyl-prop-2'-en-1'-yl)-N-hydroxyethyl benzamide (Compound 6)

Obtained by the palladium coupling reaction starting from 2-bromopropene and subsequent conversion to the amide. Preparative HPLC purification (eluent: water and CH3CN/water (50/50), gradient 80/20 to 30/70 over 50 minutes, flowrate 100 mL/minute) as above.

$^1$H NMR (300 MHz, CDCl3): $\delta$=7.73, 7.26 (2d, 4H, Ar), 6.58 (bs, 1H, NH), 4.84, 4.73 (m, 2H, HC=C), 3.86 (bt, J=5.0 Hz, 2H, —CH2OH), 3.67 (dr, J=4.0 Hz, J=5.0 Hz, 2H, —CH2NH), 3.37 (s, 2H, CH2Ar), 1.68 (bs, 3H, Me). $^{13}$C NMR (125 MHz, CDCl3): $\delta$=168.6 (1C, C=O), 144.1, 143.7 (2C, C=C, ipso-C aro), 131.8 (1C, ipso-C aro), 128.9, 127.0 (4C, Ar), 112.4 (1C, HC=C), 61.7 (1C, —CH2OH), 44.2 (1C, CH2Ar), 42.7 (1C, —CH2NH), 21.9 (1C, Me). HRMS calcd for C13H18NO2 (M+H)+ 220.1338, found 220.1340.

EXAMPLE 3

4-(2'-Methyl-but-2'-en-1'-yl)-N-hydroxyethyl benzamide (Compounds 7 and 8)

Obtained by the palladium coupling reaction starting from 2-bromo-2-butene and subsequent conversion to the amide. Purification and separation of the stereoisomers by preparative HPLC (eluent: water and CH3CN/water (50/50), gradient 70/30 to 20/80 over 50 minutes, flowrate 100 mL/minute), the Z-isomer was eluted first.

A. (Z) -4-(2'-Methyl-but-2'-en-1'-yl) -N-hydroxyethyl benzamide (Compound 7)

$^1$H NMR (300 MHz, CDCl3): $\delta$=7.71, 7.25 (2d, 4H, Ar), 6.56 (bs, 1H, NH), 5.43 (qq, J=1.26 Hz, J=7.0 Hz, 1H, HC=C), 3.86 (t, J=5.0 Hz, 2H, —CH2OH), 3.64 (q, J=5.0 Hz, 2H, —CH2NH), 3.43 (s, 2H, CH2Ar), 1.74 (dq, J=6.8 Hz, J=1.3 Hz, 3H, Me), 1.60 (m, 3H, Me). $^{13}$C NMR (125 MHz, CDCl3): $\delta$=168.6 (1C, C=O), 144.4 (1C, ipso-C aro), 133.8 (1C, C=C), 131.5 (1C, ipso-C aro), 128.6, 127.0 (4C, Ar), 120.9 (1C, HC=C), 62.1 (1C, —CH2OH), 42.7 (1C, —CH2NH), 37.2 (1C, CH2Ar), 23.2, 13.6 (2C, Me). HRMS calcd for C14H20NO2 (M+H)+ 234.1494, found 234.1495.

B. (E)-4-(2'-Methyl-but-2'-en-1'-yl)-N-hydroxyethyl benzamide (Compound 8)

$^1$H NMR (300 MHz, CDCl3): $\delta$=7.71, 7.25 (2d, 4H, Ar), 6.57 (bs, 1H, NH), 5.33 (qq, J=1.47 Hz, J=7.1 Hz, 1H, HC=C), 3.86 (t, J=5.0 Hz, 2H, —CH2OH), 3.64 (q, J=5.0 Hz, 2H, —CH2NH), 3.33 (s, 2H, CH2Ar), 1.63 (dq, J=7.0 Hz, J=1.5 Hz, 3H, Me), 1.53 (m, 3H, Me). $^{13}$C NMR (125 MHz, CDCl3): $\delta$=168.7 (1C, C=O), 144.7 (1C, ipso-C aro), 134.3 (1C, C=C), 131.7 (1C, ipso-C aro), 129.0, 126.9 (4C, Ar), 121.2 (1C, HC=C), 62.4 (1C, —CH2OH), 45.9 (1C, CH2Ar), 42.8 (1C, —CH2NH), 15.5, 13.5 (2C, Me). HRMS calcd for C14H20NO2 (M+H)+ 234.1494, found 234.1495.

EXAMPLE 4

(Z)-4-(But-2'-en-1'-yl)-N-hydroxyethyl benzamide (Compound 10)

Obtained by the palladium coupling reaction starting from cis-1-bromo-1-propene and subsequent conversion to the amide. The double bond was partially isomerized to give 4-(but-1'-en-1'-yl)-N-hydroxyethyl benzamide (15). Purification and separation of the isomeres by preparative HPLC (eluent: water and CH3CN/water (50/50), gradient 80/20 to 30/70 over 50 minutes, flow-rate 100 mL/minute), Compound 10 was eluted first.

$^1$H NMR (300 MHz, CDCl$_3$): δ=7.73, 7.27 (2d, 4H, Ar), 6.66 (bs, 1H, NH), 5.70-5.50 (m, 2H, HC=C), 3.86 (t, J=5.0 Hz, 2H, —CH$_2$OH), 3.65 (q, J=5.0 Hz, 2H, —CH$_2$NH), 3.45 (bd, J=6.8 Hz, 2H, CH$_2$Ar), 2.57 (bs, 1H, OH), 1.73 (dq, J=6.8 Hz, J=1.0 Hz, 3H, Me). $^{13}$C NMR (125 MHz, CDCl$_3$): δ=168.6 (1C, C=O), 145.2, 131.5 (2C, ipso-C aro), 128.4, 127.1 (4C, Ar), 127.9, 125.5 (2C, HC=C), 61.8 (1C, —CH$_2$OH), 42.7 (1C, —CH$_2$NH), 32.9 (1C, CH$_2$Ar), 12.8 (1C, Me). HRMS calcd for C$_{13}$H$_{18}$NO$_2$ (M+H)$^+$ 220.1338, found 220.1340.

EXAMPLE 5

4-(But-1'-en-1'-yl)-N-hydroxyethyl benzamide (Compound 15)

Isolated during preparative HPLC-purification of Compound 10 as sideproduct due to partial isomerization of Compound 10. $^1$H NMR (300 MHz, CDCl$_3$): δ=7.74, 7.41 (2d, 4H, Ar), 6.55 (bs, 1H, NH), 6.41 (m, 2H, HC=C), 3.86 (t, J=5.0 Hz, 2H, —CH$_2$OH), 3.65 (dr, J=4.0 Hz, J=5.0 Hz, 2H, —CH$_2$NH), 2.27 (ddq, J=2.0 Hz, J=4.5 Hz, J=7.2 Hz, 1H, CH$_2$), 1.11 (t, J=7.2 Hz, 3H, Me). $^{13}$C NMR (125 MHz, CDCl$_3$): δ=168.4 (1C, C=O), 141.3 (1C, ipso-C aro), 135.1 (1C, C=C), 131.9 (1C, ipso-C aro), 127.9 (1C, HC=C), 127.3, 125.9 (4C, Ar), 62.2 (1C, —CH$_2$OH), 42.8 (1C, —CH$_2$NH), 26.1 (1C, CH$_2$), 13.4 (1C, Me). HRMS calcd for C$_{13}$H$_{18}$NO$_2$ (M+H)$^+$ 220.1338, found 220.1340.

EXAMPLE 6

Synthesis of 4-(2',3'-Dimethyl-but-2'-en-1'-yl)-N-hydroxyethyl benzamide (Compound 9)

Ethyl 2-methylacetoacetate (6.8 mL, 6.9 g, 48 mmol) was added to a suspension of NaH (2.2 g, 60 percent suspension in oil) in 100 mL absolute EtOH. After 45 minutes, methyl 4-(bromomethyl)benzoate (Compound 21, 10 g, 44 mmol) was added as a solid which dissolved on slight warming. After an additional 15 minutes (1 hour total) the formation of a fine white percipitate of NaBr is noted. The reaction was stopped 10 minutes later (70 minutes total) by the addition of 50 mL saturated NH$_4$Cl solution. After evaporation of the ethanol, Compound 22 was extracted with dichloromethane and purified by chormatography on silica gel (hexane/ethyl acetate 80/20), yield 12.0 g (41 mmol, 94 percent).

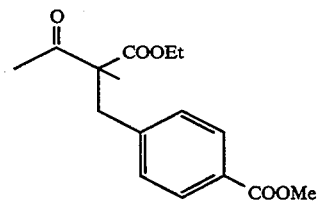

$^1$H NMR (300 MHz, CDCl$_3$) for 22: δ=7.94, 7.19 (2d, 4H, Ar), 4.27-4.11 (m, 2H, OCH$_2$), 3.91 (s, 3H, OMe), 3.34, 3.09 (d, J=13.8 Hz, 2H, —CH$_2$Ar), 2.19 (s, 3H, MeC(O)), 1.31 (s, 3H, Me), 1.27 (t, J=7.0 Hz, 3H, Me).

The ester (Compound 22, 3.2 9) was dissolved in 25 mL HOAc, then 6 mL concentrated HCl were added and the mixture heated to reflux (120° C.) for 16 hours. After removal of water and acid by repeated coevaporation with toluene, Compound 23 was obtained as a white powder in quantitative yield.

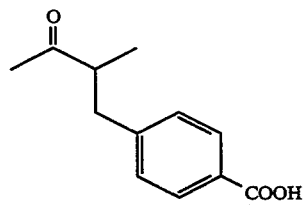

$^1$H NMR (300 MHz, CDCl$_3$) for 23: δ=8.04, 7.20 (2d, 4H, Ar), 3.09 (dd, J=7.0 Hz, J=13.5 Hz, 1H, —CH$_2$Ar), 3.65 (sextet, J=7.3 Hz, 1H, —CH), 2.63 (dd, J=7.5 Hz, J=13.5 Hz, 1H, CH$_2$Ar), 1.12 (d, J=7.0 Hz, 3H, Me).

To a solution of the crude acid (Compound 23, 10.9 mmol) in 150 mL absolute THF at zero degrees C, a 3.0M solution of methyl magnesium bromide (16.3 mL, 48 mmol) was added. After one hour at room temperature, the solution was poured on a 3 to 1 mixture of ice and concentrated HCl, and extracted three times with dichloromethane. The organic phase was washed with brine, dried over sodium sulfate and the dichlormethane removed under vacuum to provide 2.04 9 (9.2 mmol, 84 percent) of crude 4-(3'-hydroxy-2',3'-dimethyl-but-2'-en-1'-yl) benzoic acid (Compound 24). Heating Compound 24 in 30 mL absolute. EtOH in the presence of catalytic amounts of SOCl$_2$ (12 drops) gave ethyl 4-(2',3'-dimethyl-but-2'-en-1'-yl) benzoate (25), which was isolated and purified by chromatography on silica gel (hexane/ethyl acetate 95/5), yield 0.47 g (27 percent).

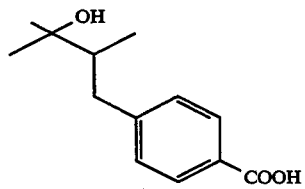

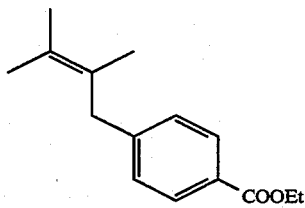

This product was converted to the amide as described above. The alkene 9 was purified by preparative HPLC (eluent: water and CH₃CN/water (50/50), gradient 60/40 to 10/90 over 50 minutes, flowrate 100 mL/minute), removing small amounts of the isomeric terminal alkene Compound 26 (eluted first, followed by Compound 9) formed at the stage of water elimination by heating in ethanol/SOCl₂.

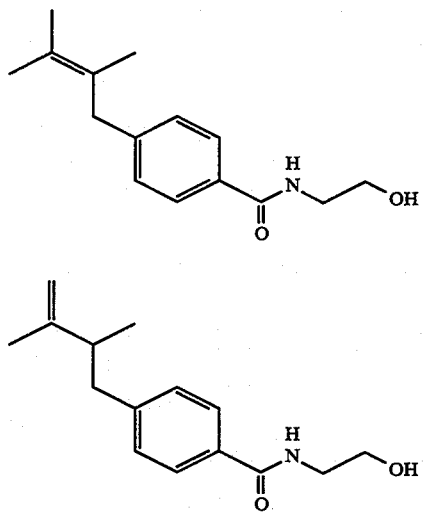

4-(2',3'-Dimethyl-but-2'-en-1'-yl)-N-hydroxyethyl benzamide (Compound 9)

¹H NMR (300 MHz, CDCl₃): δ=7.70, 7.21 (2d, 4H, Ar), 6.55 (bs, 1H, NH), 3.88–3.82 (m, 2H, —CH₂OH), 3.65–3.61 (m, 2H, —CH₂NH), 3.44 (s, 2H, CH₂Ar), 2.58 (bs, 1H, OH), 1.80, 1.75 (2bs, 6H, Me), 1.58 (s, 3H, Me). ¹³C NMR (125 MHz, CDCl₃): δ=168.7 (1C, C=O), 145.2 (1C, ipso-C aro), 131.4 (1C, ipso-C aro), 128.4, 127.0 (4C, Ar), 126.4, 125.5 (2C, C=C), 61.7 (1C, —CH₂OH), 42.7 (1C, —CH₂NH), 39.9 (1C, CH₂Ar), 20.6, 20.5, 18.3 (3C, Me). HRMS calcd for C₁₅H₂₂NO₂ (M+H)+ 248.1651, found 48.1650.

Analytical Data for the Epoxides

The alkene was dissolved in dichloromethane, then solid sodium bicarbonate and an excess of m-chloroperbenzoic acid was added. The reaction was checked for conversion, which was usually complete after 15 minutes. Water was added to remove most of the benzoic acid by extraction. The epoxides were further purified by chromatography on silicagel (eluent ethyl acetate/acetonitrile 90/10).

4-(1'-Cyclopentylmethyl-2',3'-epoxy)-N-hydroxyethyl benzamide (Compound 5)

¹H NMR (300 MHz, CDCl₃): δ=7.73, 7.32 (2d, 4H, Ar), 6.56 (bs, 1H, NH), 3.86 (t, J=5.0 Hz, 2H, —CH₂OH), 3.69–3.61 (m, 2H, —CH₂NH), 3.27 (s, 1H, CH epoxy), 3.15, 3.07 (2d, J=14.5 Hz, 2H, CH₂Ar; AB-system), 2.03–1.91, 1.86–1.75, 1.52–1.38 (3m, 6H, 3*CH₂ cyclopentane). HRMS calcd for C₁₅H₂₀NO₃ (M+H)+ 262.1443, found 262.1440.

4-(2',3'-Epoxy-prop-1'-yl)-N-hydroxyethyl benzamide (Compound 11)

¹H NMR (300 MHz, CDCl₃): δ=7.75, 7.32 (2d, 4H, Ar), 6.60 (bs, 1H, NH), 3.90 (t, J=5.0 Hz, 2H, —CH₂OH), 3.68–3.62 (m, 2H, —CH₂NH), 2.94 (s, 2H, CH₂Ar), 2.64 (s, 2H, CH epoxide), 1.29 (s, 3H, Me). ¹³C NMR (125 MHz, CDCl₃): δ=168.5 (1C, C=O), 141.1 (1C, ipso-C aro), 132.4 (1C, ipso-C aro), 129.8, 127.0 (4C, Ar), 62.1 (1C, —CH₂OH), 57.0 (1C, epoxide quart.), 53.2 (1C, epoxide sec.), 42.8, 42.6 (2C, —CH₂NH, CH₂Ar), 20.9 (1C, Me). HRMS calcd for C₁₃H₁₈NO₃ (M+H)+ 236.1287, found 236.1290.

4-(2'-Methyl-2',3'-epoxy-but-1'-yl)-N-hydroxyethyl benzamide (Compounds 12 and 13)

A mixture of (Z)-4-(2'-methyl-but-2'-en-1'-yl)-N-hydroxyethyl benzamide (Compound 7) and (E)-4-(2'-methyl-but-2+-en-1'-yl)-N-hydroxyethyl benzamide (Compound 8) was used for the preparation of the two isomeric epoxides that subsequently were separated by preparative HPLC (eluent: water and CH₃CN/water (50/50), gradient 90/10 to 40/60 over 50 minutes, flowrate 100 mL/minute). The Z-alkene 7 gave epoxide 12, which was eluted first on this HPLC separation, whereas the E-alkene 8 gave epoxide 13.

(S,R)- and (R,S)-4-(2'-Methyl-2',3'-epoxy-but-1'-yl)-N-hydroxyethyl benzamide (Compound 12)

¹H NMR (300 MHz, CDCl₃): δ=7.75, 7.34 (2d, 4H, Ar), 6.61 (bs, 1H, NH), 3.90–3.83 (m, 2H, —CH₂OH), 3.69–3.62 (m, 2H, —CH₂NH), 2.99 (q, J=5.5 Hz, 1H, CH epoxide), 2.93, 2.87 (2d, J=14.0 Hz, 2H, CH₂Ar; AB-system), 1.46 (d, J=5.5 Hz, 3H, Me), 1.18 (s, 3H, Me). ¹³C NMR (125 MHz, CDCl₃): δ=168.4 (1C, C=O), 141.8 (1C, ipso-C aro), 132.4 (1C, ipso-C aro), 129.6, 127.2 (4C, Ar), 62.4 (1C, —CH₂OH), 60.9 (1C, epoxide quart.), 60.1 (1C, epoxide tert.), 42.8 (1C, —CH₂NH), 38.5 (1C, CH₂Ar), 22.0, 14.5 (2C, Me). Anal. Calcd for C₁₄H₁₉NO₃ (249.3): C, 67.45; H, 7.68; N, 5.62. Found: C, 67.47; H, 7.78; N, 5.77. HRMS calcd for C₁₄H₂₀NO₃ (M+H)+ 250.1443, found 250.1440.

(S,S)- and (R,R)-4-(2'-Methyl-2',3'-epoxy-but-1'-yl)-N-hydroxyethyl benzamide (Compound 13)

¹H NMR (300 MHz, CDCl₃): δ=7.73, 7.30 (2d, 4H, Ar), 6.62 (bs, 1H, NH), 3.88–3.82 (m, 2H, —CH₂OH), 3.68–3.61 (m, 2H, —CH₂NH), 2.95–2.81 (m, 3H, CH epoxide, CH₂Ar), 1.30 (d, J=5.5 Hz, 3H, Me), 1.20 (s, 3H, Me). ¹³C NMR (125 MHz, CDCl₃): δ=168.4 (1C, C=O), 141.1, 132.3 (2C, ipso-C aro), 129.6, 127.0 (4C, Ar), 61.6 (1C, —CH₂OH), 60.6 (1C, epoxide quart.), 58.4 (1C, epoxide tert.), 44.2 (1C, CH₂Ar), 42.7 (1C, —CH₂NH), 16.3, 13.9 (2C, Me). HRMS calcd for C₁₄H₂₀NO₃ (M+H)+250.1443, found 250.1440.

4-(2',3'-Dimethyl-2',3'-epoxy-but-1'-yl)-N-hydroxyethyl benzamide (14)

¹H NMR (300 MHz, CDCl₃): δ=7.73, 7.29 (2d, 4H, Ar), 6.78 (bs, 1H, NH), 3.83 (t, J=5.0 Hz, 2H, —CH- $_2$OH), 3.62 (bq, J=5.0 Hz, 2H, —CH$_2$NH), 3.00, 2.94 (2d, J=15.0 Hz, 2H, CH$_2$Ar), 1.47, 1.36, 1.19 (3s, 9H, Me). $^{13}$C NMR (125 MHz, CDCl$_3$): δ=168.5 (1C, C=O), 142.2 (1C, ipso-C aro), 132.2 (1C, ipso-C aro), 129.4, 127.1 (4C, Ar), 64.5 (1C, epoxide), 62.4 (1C, —CH$_2$OH), 42.8 (1C, —CH$_2$NH), 40.6 (1C, CH$_2$Ar), 21.43, 21.40, 18.4 (3C, Me). It was not possible to assign the second quarternery oxirane carbon. HRMS calcd for C$_{15}$H$_{22}$NO$_3$ (M+H)+ 264.1600, found 264. 1600.

The foregoing is intended as illustrative of the present invention but not limiting. Numerous variations and modifications can be effected without departing from the true spirit and scope of the invention.

What is claimed:

1. A process for forming an epoxide from a 1-benzyl-1-hydrocarbyl-substituted alkene substrate that comprises the steps of:
   (a) admixing in an aqueous medium containing an oxidation-effective amount of a peroxycarboximic acid a catalytically effective amount of monoclonal antibody molecules or paratope-containing portions thereof and a substrate 1-benzyl-1-hydrocarbyl alkene to which said antibody molecules or paratope-containing portions bind to form a reaction medium, said substrate bound by said monoclonal antibody molecules or the paratope-containing portions thereof containing up to about 25 carbon atoms bonded to the carbon atoms of the alkenyl double bond including said 1-hydrocarbyl substituent and the phenyl ring of said 1-benzyl substituent, said monoclonal antibodies or paratope-containing portions also binding to an analog ligand that is an analog of said substrate, said analog ligand being an N-benzyl-N-hydrocarbyl-piperidinium compound in which the nitrogen atom of the piperidinium compound analog ligand is analogous to the 1-carbon atom of the alkene substrate, said analog ligand containing no more ring structures bonded to the piperidinium ring than are present in said substrate; and
   (b) maintaining said reaction mixture under biological reaction conditions for a time period sufficient for said substrate to be converted to a corresponding epoxide.

2. The process according to claim 1 wherein said peroxycarboximic acid is formed in situ by the reaction of hydrogen peroxide on a C$_1$-C$_3$ nitrile.

3. The process according to claim 1 wherein said substrate has a structure that corresponds to the formula

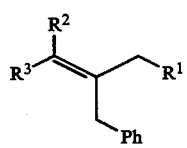

in which Ph is phenyl,
R$^1$ is hydrocarbyl, R$^2$ and R$^3$ are each independently hydrogen or hydrocarbyl, or R$^1$ and R$^2$ together with their intervening atoms and vinyl group form a monocyclic, bicyclic or tricyclic ring structure.

4. The process according to claim 3 wherein said analog of said substrate has a structure that corresponds to the formula

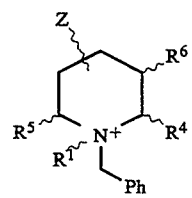

wherein R$^4$, R$^5$ and R$^6$ are independently hydrogen or hydrocarbyl groups or R$^4$ and R$^6$ together form a monocyclic, bicyclic or tricyclic ring structure, and the sum of the carbon atoms in R$^1$, R$^4$, R$^5$ and R$^6$ and the depicted benzyl group and the atoms of the depicted piperidinium ring, exclusive of Z is up to about 30, and Z is a carboxyl-terminated linking group for bonding the analog ligand to an immunogenic carrier that is amide-, amidomethyl- or ester-linked to the analog ligand at a piperidinium ring position between R$^5$ and R$^6$.

5. A process for forming an epoxide from a 1-benzyl-1-hydrocarbyl-substituted alkene substrate that comprises the steps of:
   (a) admixing in an aqueous medium containing
      (i) an oxidation-effective amount of a peroxycarboximic acid formed in situ by the reaction of hydrogen peroxide and a C$_1$-C$_3$ nitrile,
      (ii) a catalytically effective amount of monoclonal antibody molecules or paratope-containing portions thereof, and
      (iii) a substrate 1-benzyl-1-hydrocarbyl alkene to which said antibody molecules or paratope-containing portions bind to form a reaction medium, the structure of said substrate bound by said monoclonal antibody molecules or the paratope-containing portions thereof corresponding to the formula

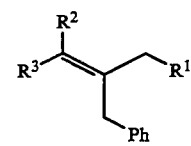

in which Ph is phenyl,
R$^1$ is hydrocarbyl, R$^2$ and R$^3$ are each independently hydrogen or hydrocarbyl, or R$^1$ and R$^2$ together with their intervening atoms and vinyl group form a monocyclic, bicyclic or tricyclic ring structure;
said monoclonal antibodies or paratope-containing portions also binding to an analog ligand that is an analog of said substrate, said analog ligand having a structure that corresponds to the formula

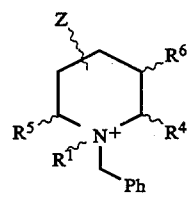

wherein R$^4$, R$^5$ and R$^6$ are independently hydrogen or hydrocarbyl groups or R$^4$ and R$^6$ together form a monocyclic, bicyclic or tricyclic ring structure, and the sum of the carbon atoms in $R^1$, $R^4$, $R^5$ and $R^6$ and the depicted benzyl group and the atoms of the depicted piperidinium ring, exclusive of Z is up to about 30, and Z is a carboxy-terminated linking group for bonding the analog ligand to an immunogenic carrier that is amide-, amidomethyl- or ester-linked to the analog ligand at a piperidinium ring position between $R^5$ and $R^6$; and (b) maintaining said reaction mixture under biological reaction conditions for a time period sufficient for the alkene moiety of said substrate to be converted to an epoxide.

6. The process according to claim 5 including the further step of recovering the corresponding epoxide product.

7. The process according to claim 5 wherein said $C_1$-$C_3$ nitrile is acetonitrile.

8. The process according to claim 7 wherein said monoclonal antibodies or paratope-containing portions thereof are secreted by Hybridoma 20B11.

9. The process according to claim 7 wherein the phenyl ring of said analog ligand contains a substituent selected from the group consisting of halo, nitro, carboxyl, $C_1$-$C_6$ alkyl carboxylate, carboxamido, N-mono-$C_1$-$C_6$ alkyl carboxamido, N,N-di-$C_1$-$C_6$ alkyl carboxamido, N-(hydroxyethyl)carboxamido and N,N-di-(hydroxyethyl)carboxamido groups.

10. The process according to claim 9 wherein said analog ligand has a structure that corresponds to the formula

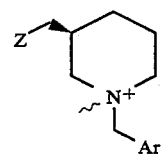

wherein Ar is a 4-(N-hydroxyethyl)benzamido group.

* * * * *